(12) United States Patent
Valenzuela et al.

(10) Patent No.: US 6,846,914 B2
(45) Date of Patent: Jan. 25, 2005

(54) TIE-2 LIGAND-3

(75) Inventors: David M. Valenzuela, Yorktown Heights, NY (US); Pamela F. Jones, Leeds (GB); George D. Yancopoulos, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 337 days.

(21) Appl. No.: 10/215,224

(22) Filed: Aug. 8, 2002

(65) Prior Publication Data

US 2003/0059887 A1 Mar. 27, 2003

Related U.S. Application Data

(60) Division of application No. 09/202,491, filed as application No. PCT/US97/10728 on Jun. 19, 1997, now Pat. No. 6,432,667, which is a continuation-in-part of application No. 08/665,926, filed on Jun. 19, 1996, now Pat. No. 5,851,797.
(60) Provisional application No. 60/022,999, filed on Aug. 2, 1996, and provisional application No. 60/021,087, filed on Jul. 2, 1996.

(51) Int. Cl.$^7$ ............................................. C07K 14/475
(52) U.S. Cl. ...................... 530/402; 530/350; 435/23.5; 435/23.1; 424/1.41
(58) Field of Search ................................ 530/350, 402; 435/23.5, 23.1; 424/1.41

(56) References Cited

U.S. PATENT DOCUMENTS

| 5,332,671 A | 7/1994 | Ferrara et al. |
| 5,447,860 A | 9/1995 | Ziegler |
| 5,521,073 A | * 5/1996 | Davis et al. |

FOREIGN PATENT DOCUMENTS

| WO | WO 94/11499 | 5/1994 |
| WO | WO 96/11269 | 4/1996 |
| WO | WO 9620403 A1 * | 7/1996 |
| WO | WO 96/31598 | 10/1996 |

OTHER PUBLICATIONS

Valenzuela et al., Angiopoietins 3 and 4: Diverging gene counterparts in mice and humans,Proc. Natl. Acad. Sci. USA, 96(5):1094–1909, Mar. 1999.*
Biochemical and Biophysical Research Communications, vol. 195, No. 1, issued Aug. 31, 1993, Iwama et al., "Molecular Cloning and Characterization of Mouse *TIE* and *TEK* Receptor Tyrosine Kinase Genes and Their Expression in Hematopoietic Stem Cell", pp. 301–309.
BLOOD, vol. 80, No. 10, issued Nov. 15, 1992, Korhonen et al.,"Enhanced Expression of the *tie* Receptor Tyrosine Kinase in Endothelial Cells During Neovascularization", pp. 2548–2555.
BLOOD, vol. 87, No. 1, issued Jan. 1, 1996, Hashiyama et al., "Predominant Expression of a Receptor Tyrosine Kinase, TIE, in Hematopoietic Stem Cells and B Cells", pp. 93–101.
BLOOD, vol. 87, No. 6, issued Mar. 15, 1996, Batard et al., "The Tie Receptor Tyrosine Kinase Is Expressed by Hematopoietic Progenitor Cells and by a Subset of Megakaryocytic Cells", pp. 2212–2220.
Cell, vol. 87, issued Dec. 27, 1996, Davis et al., "Isolation of Angiopoietin–1 a Ligand for the TIE2 Receptor by Secretion–Trap Expression Cloning", pp. 1161–1169.
Cell, vol. 87, issued Dec. 27, 1996, Suri et al., "Requisite Role of Angiopoietin–1, a Ligand for the TIE2 Receptor, during Embryonic Angiogenesis", pp. 1171–1180.
Molecular and Cellular Biology, vol. 12, No. 14, issued Apr. 1992, Partanen et al., "A Novel Endothelial Cell Surface Receptor Tyrosine Kinase with Extracellular Epidermal Growth Factor Homology Domains", pp. 1698–1707.
Nature, vol. 386, No. 6, issued Jul 6, 1995, Sato et al., "Distinct roles of the receptor tryosine kinases Tie–1 and Tie–2 in blood vessel formation", pp. 70–74.
Oncogene, vol. 8, 1993, Dumont et al., " The endothelial- –specific receptor tyrosine kinase, tek, is a member of a new subfamily of receptors", pp. 1293–1301.
Oncogene, vol. 8, 1993, Maisonpierre et al., "Distinct rat genes with related profiles of expression define TIE receptor tyrosine kinase family", pp. 1631–1637.
Proc. Natl. Acad. Sci., vol. 87, issued Nov. 1990, Partanen et al., "Putative tyrosine kinases expressed in K562 human leukemia cells", pp. 8913–8917.
Proc. Natl. Acad. Sci., vol. 90, issued Oct. 1993, Sato et al.,"tie–1 and tie–2 define another class of putative receptor tyrosine kinase genes expressed in early embryonic vascular system", pp. 9355–9358.

* cited by examiner

*Primary Examiner*—Lorraine Spector
*Assistant Examiner*—Claire M. Kaufman
(74) *Attorney, Agent, or Firm*—Valeta Gregg, Esq.

(57) ABSTRACT

The present invention provides for an isolated nucleic acid molecule encoding a member of the TIE ligand family. The present invention also provides for an isolated nucleic acid molecule encoding TIE ligand-3 or TIE ligand-4. In addition, the invention provides for a receptorbody which specifically binds TIE ligand-3 or TIE ligand-4. The invention also provides an antibody which specifically binds TIE ligand-3 or TIE ligand-4. The invention further provides for an antagonist of TIE. The invention also provides for therapeutic compositions as well as a method of blocking blood vessel growth, a method of promoting neovascularization, a method of promoting the growth or differentiation of a cell expressing the TIE receptor, a method of blocking the growth or differentiation of a cell expressing the TIE receptor and a method of attenuating or preventing tumor growth in a human.

7 Claims, 10 Drawing Sheets r EHK-1 ecto / h IgG1 Fc
Gelfoam (6 ug)

r TIE-2 ecto / h IgG1 Fc
Gelfoam (6 ug)

Fig. 6A

```
         10          20          30          40          50          60          70          80          90
CTGTCCTGGT ACCTGACAAG ACCACCTCAC CACCACTTGG TCTCAG ATG CTC TGC CAG CCA GCT ATG CTA CTA GAT GGC CTC CTC CTG CTG
                                                    M   L   C   Q   P   A   M   L   L   D   G   L   L   L   L>

100         110         120         130         140         150         160         170
GCC ACC ATG GCT GCA GCC CAG CAC AGA GGG CCA GAA GCC GGT GGG CAC CGC CAG ATT CAC CAG GTC CGG CGT GGC CAG TGC AGC
 A   T   M   A   A   A   Q   H   R   G   P   E   A   G   G   H   R   Q   I   H   Q   V   R   R   G   Q   C   S>

180         190         200         210         220         230         240         250
TAC ACC TTT GTG GTG CCG GAG CCT GAT ATC TGC CAG CTG GCG CCG ACA GCG GCG CCT GAG GCT TTG GGG GGC TCC AAT AGC CTC
 Y   T   F   V   V   P   E   P   D   I   C   Q   L   A   P   T   A   A   P   E   A   L   G   G   S   N   S   L>

260         270         280         290         300         310         320         330         340
CAG AGG GAC TTG CCT GCC TCG AGG CTG CAC CTA ACA GAC TGG CGA GCC CAG AGG GCC CAG CGG GCC CAG CGT GTG AGC CAG CTG
 Q   R   D   L   P   A   S   R   L   H   L   T   D   W   R   A   Q   R   A   Q   R   A   Q   R   V   S   Q   L>

350         360         370         380         390         400         410         420
GAG AAG ATA CTA GAG AAT AAC ACT CAG TGG CTG CTG AAG CTG GAG CAG TCC ATC AAG GTG AAC TTG AGG TCA CAC CTG GTG CAG
 E   K   I   L   E   N   N   T   Q   W   L   L   K   L   E   Q   S   I   K   V   N   L   R   S   H   L   V   Q>

430         440         450         460         470         480         490         500         510
GCC CAG CAG GAC ACA ATC CAG AAC CAG ACA ACT ACC ATG CTG GCA CTG GGT GCC AAC CTC ATG AAC CAG ACC AAA GCT CAG ACC
 A   Q   Q   D   T   I   Q   N   Q   T   T   T   M   L   A   L   G   A   N   L   M   N   Q   T   K   A   Q   T>

520         530         540         550         560         570         580         590
CAC AAG CTG ACT GCT GTG GAG GCA CAG GTC CTA AAC CAG ACA TTG CAC ATG AAG ACC CAA ATG CTG GAG AAC TCA CTG TCC ACC
 H   K   L   T   A   V   E   A   Q   V   L   N   Q   T   L   H   M   K   T   Q   M   L   E   N   S   L   S   T>

600         610         620         630         640         650         660         670
AAC AAG CTG GAG CGG CAG ATG CTG ATG CAG AGC CGA GAG CTG CAG CGG CTC CAG GGT CGC AAC AGG GCC CTG GAG ACC AGG CTG
 N   K   L   E   R   Q   M   L   M   Q   S   R   E   L   Q   R   L   Q   G   R   N   R   A   L   E   T   R   L>

680         690         700         710         720         730         740         750         760
CAG GCA CTG GAA GCA CAA CAT CAG GCC CAG CTT AAC AGC CTC CAA GAG AAG AGG GAA CAA CTG CAC AGT CTC CTG GGC CAT CAG
 Q   A   L   E   A   Q   H   Q   A   Q   L   N   S   L   Q   E   K   R   E   Q   L   H   S   L   L   G   H   Q>

770         780         790         800         810         820         830         840
ACC GGG ACC CTG GCT AAC CTG AAG CAC AAT CTG CAC GCT CTC AGC AGC AAT TCC AGC TCC CTG CAG CAG CAG CAG CAG CAA CTG
 T   G   T   L   A   N   L   K   H   N   L   H   A   L   S   S   N   S   S   S   L   Q   Q   Q   Q   Q   Q   L>

850         860         870         880         890         900         910         920         930
ACG GAG TTT GTA CAG CGC CTG GTA CGG ATT GTA GCC CAG GAC CAG CAT CCG GTT TCC TTA AAG ACA CCT AAG CCA GTG TTC CAG
 T   E   F   V   Q   R   L   V   R   I   V   A   Q   D   Q   H   P   V   S   L   K   T   P   K   P   V   F   Q>

940         950         960         970         980         990         1000        1010
GAC TGT GCA GAG ATC AAG CGC TCC GGG GTT AAT ACC AGC GGT GTC TAT ACC ATC TAT GAG ACC AAC ATG ACA AAG CCT CTC AAG
 D   C   A   E   I   K   R   S   G   V   N   T   S   G   V   Y   T   I   Y   E   T   N   M   T   K   P   L   K>

1020        1030        1040        1050        1060        1070        1080        1090
GTG TTC TGT GAC ATG GAG ACT GAT GGA GGT GGC TGG ACC CTC ATC CAG CAC CGG GAG GAT GGA AGC GTA AAT TTC CAG AGG ACC
 V   F   C   D   M   E   T   D   G   G   G   W   T   L   I   Q   H   R   E   D   G   S   V   N   F   Q   R   T>

1100        1110        1120        1130        1140        1150        1160        1170        1180
TGG GAA GAA TAC AAA GAG GGT TTT GGT AAT GTG GCC AGA GAG CAC TGG CTG GGC AAT GAG GCT GTG CAC CGC CTC ACC AGC AGA
 W   E   E   Y   K   E   G   F   G   N   V   A   R   E   H   W   L   G   N   E   A   V   H   R   L   T   S   R>

1190        1200        1210        1220        1230        1240        1250        1260
ACG GCC TAC TTG CTA CGC GTG GAA CTG CAT GAC TGG GAA GGC CGC CAG ACC TCC ATC CAG TAT GAG AAC TTC CAG CTG GGC AGC
 T   A   Y   L   L   R   V   E   L   H   D   W   E   G   R   Q   T   S   I   Q   Y   E   N   F   Q   L   G   S>

1270        1280        1290        1300        1310        1320        1330        1340        1350
GAG AGG CAG CGG TAC AGC CTC TCT GTG AAT GAC AGC AGC AGT CCA GCA GGG CGC AAG AAC AGC CTG GCT CCT CAG GGC ACC AAG
 E   R   Q   R   Y   S   L   S   V   N   D   S   S   S   P   A   G   R   K   N   S   L   A   P   Q   G   T   K>

1360        1370        1380        1390        1400        1410        1420        1430
TTC AGC ACC AAA GAC ATG GAC AAT GAT AAC TGC ATG TGT AAA TGT GCT CAG ATG CTG TCT GGA GGC TGG TGG TTT GAT GCC TGT
 F   S   T   K   D   M   D   N   D   N   C   M   C   K   C   A   Q   M   L   S   G   G   W   W   F   D   A   C>
```

Fig. 6B

```
        1440       1450       1460       1470       1480       1490      1500       1510
GGC CTC TCC AAC CTC AAT GGC ATC TAC TAT TCA GTT CAT CAG CAC TTG CAC AAG ATC AAT GGC ATC CGC TGG CAC TAC TTC CGA
 G   L   S   N   L   N   G   I   Y   Y   S   V   H   Q   H   L   H   K   I   N   G   I   R   W   H   Y   F   R>
 1520      1530       1540      1550       1560       1570      1580       1590       1600
GGC CCC AGC TAC TCA CTG CAC GGC ACA CGC ATG ATG CTG AGG CCA ATG GGT GCC TGA CACA CAGCCCTGCA GAGACTGATG
 G   P   S   Y   S   L   H   G   T   R   M   M   L   R   P   M   G   A   *>
         1610      1620       1630       1640      1650       1660       1670      1680       1690      1700
CCGTAGGAGG ATTCTCAACC CAGGTGACTC TGTGCAGGCT GGGCCCTGCC CAGAAATCAG TGCCCAGGGC TCATCTTGAC ATTCTGGAAC ATCGGAACCA
         1710      1720       1730       1740      1750       1760       1770      1780       1790      1800
GCTTACCTTG CCCCTGAATT ACAAGAATTC ACCTGCCTCC CTGTTGCCCT CTAAATTGTGA AATTGCTGGG TGCTTGAAGG CACCTGCCTC TGTTGGAACC
         1810      1820       1830       1840
ATACTCTTTC CCCCTCCTGC TGCATGCCCG GGAATCCCTG CCATGAACT
```

Fig. 7

```
             10        20        30        40        50        60        70        80        90       100
mAng3   MLCQPAMLLDGILL-LATMAAAQHRGEAGGHRQIHQVRRGQCSYTFVVPEPDICQLAPTAAPEALGSNSLQRDLPASRLHLTDWRAQRAQRVSQLE
hAng4   ..s.l...qgs..vv...sv..qtrq..drqcetlv.qh.h.....ll.ksep.----..pg..vsrd..t....esl.np...-g-k-lpt.--.-.k...>
hAng1   .tvflsfaflaai.thigc-sn.r.s..ns.r.y-nrigh....a...il..h.g-nc-resttdqvn-t.a....a.h---ve-p-dfss--.klqh..>
mAng1   .tvflsfaffaai.thigc-sn.r.n..r.y-nrigh....a...il..h.g-nc-res..t.qyn-t.a....a.h---ve-p-dfss--.klqh..>
mAng2   .wqjiflttfgwd.v-..saysnfrksvdst.r..y-..qn.p.....ll..t.s.rs-sss.y-ms--.av..a.l--dyd-d---sv..l.v-l--.>
hAng2   .wgivfftlscd.v-..aaynnfrksmdsi.kk.y-...qh.s.....ll..m.n.rs-sss.y-vs--.av..a.l--eyd-d---sv..l.v-l--.>

110       120       130       140       150       160       170       180       190       200
mAng3   KILENNTQWLLKLEQSIKVNLRSHLVQAQQDTIQNQTTTMLALGANLMNQTKAQTKRLTAVEAQVLNQTLHMKTQMLENSLSTNKLERQMLSTNKLERQMLQSRELQRL
hAng4   qa.q......k...ra..ti....k.e.v..qma.....ap..e..ts.l-..t..ir...dm..l....sr.da..p.tf.......n.l.l.rgk..g..>
hAng1   hvm..y......q...ny.ve.mk.ema.i..nav..h.a...ei.ts.ls.ae..r...d.t.....srlei.l.........y....k.l.q.tn.ilki.>
mAng1   hvm..y......q...ny.ve.mk.ema.i..nav..h.a...ei.ts.ls.ae..r...d.t.....srlei.l.........y....k.i.q.tn.ilki.>
mAng2   n.......m......m...ny.qd.mkkem.ei..nvv......av.iei.ts.l...a..r..d.......trlei.l.qh.i.......k.i.d.ts.ink.>
hAng2   n.m.....m......m...ny.qd.mkkem.ei..nav......av.iei.t..l....ae.r..d.......trlel.l..h.........k.i.d.ts.ink.>

210       220       230       240       250       260       270       280       290       300
mAng3   QGRNRALETRLQALEAQHQAQLNSLQEKREQLISILGHQTYTLANLKHNLHALSSNNSSSLQQQQQ----QLTEFVQRLVRTVA----QDQHFVS--LK-TPKFVFQDCAEI
hAng4   ..q.s...k......tkq..ee..a.ils.kak.lnt.sr.saa.t.ierg.rgvrh....l..d..hslr..lvllth..qer.----nasa..af--im-ageт........>
hAng1   .hek.sl..hkilem.gk.kee.dt.k.ek.n.qg.vtr..yiiqe.ekq.nratt.n.v..k..l---e.mdt.hn..nlct---kegvllkgggkr-eeekp.r...dv>
mAng1   .hek.sl..hkilem.gk.kee.dt.k.ek.n.qg.vsr..fliqe.ekq.sratn.n.l..k..l---e.mdt.hn..slct---kegvllkgggkr-eeekp.r...dv>
mAng2   .nk.sf..qkvldn.gk.se...q.mk.qkde.qv.vsk.ssvide.ekk.vtatv.n.l..k..h---d.m.t.ns.ltmms-spnskss.a--irkeeqtt.r....>
hAng2   .dk.sf..kkvl.m.dk.ii..q.ik.ekd..qv.vsk.nsiiee.ckkivtatv.n.v..k..h---d.m.t.nn.ltmmstsnsakd.tv--a..eeqis.r....v>

310       320       330       340       350       360       370       380       390       400
mAng3   KRSGVNPSGVTTIYETNMTKPLKVFCLMEETLGGGWTLIQHREDGSVNFQRITWEFYKEGFGNVAREHWLGNEAVHRLTSRTAYLLRVELHDWEGRQTSIQY
hAng4   q...asa........qvs.a...l..lqss..r......r..n.t......n.kd..q....cp.g......v..q..r.a..s......g....heeyа..>
hAng1   yqa.f.k..i....in..pe.k....n.dwn......v.......ld...g.k...m....psg.y....fifai..qrg.m..i..m....nrays..>
mAng1   yqa.f.k..i....fn..pe.k....n.dwn......v.......ld...g.k...m....psg.y....fifai..qrg.m..i..m....nrays..>
mAng2   fk.lt...i..ltfp.s.eei.ay...dvg......v.......d.......k.......v....plg.y......f.sq..gghr.v.kiq.k.....neahsl.>
hAng2   fk..ht.n.i..ltfp.s.eei.ay...ag......i..r......d.......k.......v....psg.y......f.sq..nqqr.v.kih.k.....neaysl.>

410       420       430       440       450       460       470       480       490       500
mAng3   ENFQLGSERQRYSLSVNDSSSSAGHKNSLAPQQTKFSTKLMDNINCMCKCAQMLSGGWWFDACGLSNLANGIYYSVHQHLRKINGIRWHYFRGPSYSLHGTRMLRPMGA*
hAng4   .h.h...n.l.r..vgy.g....qs..vl.n.s....l.s...h.l.....vm............k.....k....rаs...i..ldi*
dr.hi.n.k.n.r.ylkghtgt..kqs..ilh.ad......a........l.t.........p.....mf.tag.nhg.l..k......k....rs.t.i..ldf*
dr.hi.n.k.n.r.ylkghtgt..kqs..ilh.ad......a........l.t.........p.....mf.tag.nhg.l..k......k....rs.t.i..ldf*
dh.y.ag..esn.rihltgligtc.akis.lsqp.sd....s..k.i..s.........p....q..pqk.ntn.f...k.y.wk.sg...ka.t.i..adf*
.h.y.s...eln.rihlkgltgt..kis.lsqp.nd.....g..k.i..s.t............p....m..pqr.ntn.f...k.y.wk.sg...ka.t.i..adf*
```

Fig.8A.

```
         10              20              30              40              50              60
ATG CTC TCC CAG CTA GCC ATG CTG CAG GGC AGC CTC CTC GTG GTT GCC ACC ATG TCT GTG GCT
 M   L   S   Q   L   A   M   L   Q   G   S   L   L   V   V   A   T   M   S   V   A 70              80              90             100             110             120              130
CAA CAG ACA AGG CAG GAG GCG GAT AGG GGC TGC GAG ACA CTT GTA GTC CAG CAC GGC CAC TGT AGC
 Q   Q   T   R   Q   E   A   D   R   G   C   E   T   L   V   V   Q   H   G   H   C   S 140             150             160             170             180             190
TAC ACC TTC TTG CTG CCC AAG TCT GAG CCC TGC CCT CCG GGG CCT GAG GTC TCC AGG GAC TCC AAC
 Y   T   F   L   L   P   K   S   E   P   C   P   P   G   P   E   V   S   R   D   S   N 200             210             220             230             240             250             260
ACC CTC CAG AGA GAA TCA CTG GCC AAC CCA CTG CAC CTG GGG AAG TTG CCC ACC CAG CAG GTG AAA
 T   L   Q   R   E   S   L   A   N   P   L   H   L   G   K   L   P   T   Q   Q   V   K 270             280             290             300             310             320             330
CAG CTG GAG CAG GCA CTG CAG AAC ACG CAG TGG CTG AAG AAG CTA GAG AGG GCC ATC AAG ACG
 Q   L   E   Q   A   L   Q   N   T   Q   W   L   K   K   L   E   R   A   I   K   T 340             350             360             370             380             390
ATC TTG AGG TCG AAG CTG GAG CAG GTC CAG CAG CAA ATG GCC CAG AAT CAG ACG GCC CCC ATG CTA
 I   L   R   S   K   L   E   Q   V   Q   Q   Q   M   A   Q   N   Q   T   A   P   M   L 400             410             420             430             440             450             460
GAG CTG GGC ACC AGC AGC CTC CTG CTC AAC CAG ACC ACT GCC CAG ATC CGC AAG CTG ACC GAC ATG GAG GCT
 E   L   G   T   S   S   L   L   L   N   Q   T   T   A   Q   I   R   K   L   T   D   M   E   A 470             480             490             500             510             520
CAG CTC CTG AAC CAG ACA TCA AGA ATG GAT GCC CAG ATG CCA GAG ACC TTT CTG TCC ACC AAC AAG
 Q   L   L   N   Q   T   S   R   M   D   A   Q   M   P   E   T   F   L   S   T   N   K 530             540             550             560             570             580             590
CTG GAG AAC CAG CTG CTG CTA CAG AGG CAG AAG CTC CAG CAG CTT CAG CTA CAA AAC AGC GCG CTC
 L   E   N   Q   L   L   L   Q   R   Q   K   L   Q   Q   L   Q   L   Q   N   S   A   L
```

Fig.8B.

```
       600         610         620         630         640         650         660
GAG AAG CGG TTG CAG GCC CTG GAG ACC AAG CAG GAG GAG CTG GCC AGC ATC CTC AGC AAG AAG
 E   K   R   L   Q   A   L   E   T   K   Q   E   E   L   A   S   I   L   S   K   K
       670         680         690         700         710         720
GCG AAG CTG CTG AAC ACG CTG AGC CGC CAG AGC GCC GCC CTC ACC AAC ATC GAG CGC GGC CTG CGC
 A   K   L   L   N   T   L   S   R   Q   S   A   A   L   T   N   I   E   R   G   L   R
       730         740         750         760         770         780         790
GGT GTC AGG CAC AAC TCC AGC CTC CAG GAC CAG CAG CAC AGC CTG CGC CAG CTG CTG GTG TTG
 G   V   R   H   N   S   S   L   Q   D   Q   Q   H   S   L   R   Q   L   L   V   L
       800         810         820         830         840         850
TTG CGG CAC CTG GTG CAA GAA AGG GCT AAC GCC TCG GCC CCG GCC TTC ATA ATG GCA GGT GAG CAG
 L   R   H   L   V   Q   E   R   A   N   A   S   A   P   A   F   I   M   A   G   E   Q
       860         870         880         890         900         910         920
GTG TTC CAG GAC TGT GCA GAG ATC CAG CGC TTC TCT GGG GCC AGT GCC AGT GGT GTC TAC ACC ATC CAG
 V   F   Q   D   C   A   E   I   Q   R   F   S   G   A   S   A   S   G   V   Y   T   I   Q
       930         940         950         960         970         980         990
CTG TCC AAT GCA ACG AAG CCC AGG AAG GTG TTC TGT GAC CTG CAG AGC AGT GGA GGC AGG TGG ACC
 L   S   N   A   T   K   P   R   K   V   F   C   D   L   Q   S   S   G   G   R   W   T
      1000        1010        1020        1030        1040        1050
CTC ATC CAG CGC CGT CAG GAG AAT GGC ACC GTG AAT TTT CAG CGG AAC TGG AAG GAT TAC AAA CAG GGC
 L   I   Q   R   R   Q   E   N   G   T   V   N   F   Q   R   N   W   K   D   Y   K   Q   G
      1060        1070        1080        1090        1100        1110        1120
TTC GGA GAC CCA GCT GGG GAG CAC TGG CTG GGC AAT GAA GTG GTG CAC CAG CTC ACC AGA AGG GCA
 F   G   D   P   A   G   E   H   W   L   G   N   E   V   V   H   Q   L   T   R   R   A
      1130        1140        1150        1160        1170        1180
GCC TAC TCT CTG CGT GTG GAG CTG CAA GAC TGG GAA GGC CAC GAG GCC TAT GCC CAG TAC GAA CAT
 A   Y   S   L   R   V   E   L   Q   D   W   E   G   H   E   A   Y   A   Q   Y   E   H
```

Fig. 8C

```
1190           1200            1210            1220            1230            1240            1250
TTC CAC CTG GGC AGT GAG AAC CAG CTA TAC AGG CTT TCT GTG GTC GGG TAC AGC GGC TCA GCA GGG
 F   H   L   G   S   E   N   Q   L   Y   R   L   S   V   V   G   Y   S   G   S   A   G
       1260            1270            1280            1290            1300            1310            1320
CGC AGC AGC AGC CTG CTG CAG AGC ACC AGC TTT GAC CTT GAC TCA GAC AAC GAC CAC TGT
 R   Q   S   S   S   L   L   Q   N   T   S   F   D   L   D   S   D   N   D   H   C
               1330            1340            1350            1360            1370            1380
CTC TGC AAG TGT GCC CAG GTG ATG TCT GGA GGG TGG TTT GAC GCC TGT GGC CTG TCA AAC CTC
 L   C   K   C   A   Q   V   M   S   G   G   W   F   D   A   C   G   L   S   N   L
       1390            1400            1410            1420            1430            1440            1450
AAC GGC GTC TAC TAC CAC GCT CCC GAC AAC AAG TAC AAG ATG GAC GGG ATC CGC TGG CAC TAC TTC
 N   G   V   Y   Y   H   A   P   D   N   K   Y   K   M   D   G   I   R   W   H   Y   F
       1460            1470            1480            1490            1500            1510
AAG GGC CCC AGC TAC TCA CTG CGT GCC TCT CGC ATG ATG ATA CGG CCT TTG GAC ATC TAA
 K   G   P   S   Y   S   L   R   A   S   R   M   M   I   R   P   L   D   I   *
```

TIE-2 LIGAND-3

This application is a Divisional Application of U.S. Ser. No. 09/202,491 filed Nov. 16, 1998, now issued as U.S. Pat. No. 6,432,667, which is a national stage application of International Patent Application PCT/US97/10728 filed Jun. 19, 1997, which is a continuation-in-part of U.S. Ser. No. 08/665,926, filed Jun. 19, 1996; U.S. Pat. No. 5,851,797 PCT/US97/10728 claims the benefit of Provisional Applications 60/022,999, filed Aug. 2, 1996, and 60/021,087 filed Jul. 2, 1996. The disclosures of these applications are herein specifically incorporated by reference in their entirety.

INTRODUCTION

The present invention relates generally to the field of genetic engineering and more particularly to genes for receptor tyrosine kinases and their cognate ligands, their insertion into recombinant DNA vectors, and the production of the encoded proteins in recipient strains of microorganisms and recipient eukaryotic cells. More specifically, the present invention is directed to novel ligands, known as TIE ligand-3 and TIE ligand-4, that bind the TIE-2 receptor, as well as to methods of making and using the novel ligands. The invention further provides nucleic acid sequences encoding TIE ligand-3 or TIE ligand-4, methods for the generation of the nucleic acids and the gene products. The novel TIE ligands, as well as nucleic acids encoding them, may be useful in the diagnosis and treatment of certain diseases involving endothelial cells and associated TIE receptors, such as neoplastic diseases involving tumor angiogenesis, wound healing, thromboembolic diseases, atherosclerosis and inflammatory diseases. In addition, the ligands may be used to promote the proliferation and/or differentiation of hematopoietic stem cells.

Biologically active ligands of the invention may be used to promote the growth, survival, migration, and/or differentiation and/or stabilization or destabilization of cells expressing TIE receptor. Biologically active TIE ligands may be used for the in vitro maintenance of TIE receptor expressing cells in culture. Cells and tissues expressing TIE receptor include, for example, cardiac and vascular endothelial cells, lens epithelium and heart epicardium and early hematopoietic cells. Alternatively, such ligands may be used to support cells which are engineered to express TIE receptor. Further, the ligands and their cognate receptors may be used in assay systems to identify agonists or antagonists of the receptor.

BACKGROUND OF THE INVENTION

The cellular behavior responsible for the development, maintenance, and repair of differentiated cells and tissues is regulated, in large part, by intercellular signals conveyed via growth factors and similar ligands and their receptors. The receptors are located on the cell surface of responding cells and they bind peptides or polypeptides known as growth factors as well as other hormone-like ligands. The results of this interaction are rapid biochemical changes in the responding cells, as well as a rapid and a long-term readjustment of cellular gene expression. Several receptors associated with various cell surfaces may bind specific growth factors.

The phosphorylation of tyrosine residues in proteins by tyrosine kinases is one of the key modes by which signals are transduced across the plasma membrane. Several currently known protein tyrosine kinase genes encode transmembrane receptors for polypeptide growth factors and hormones such as epidermal growth factor (EGF), insulin, insulin-like growth factor-I (IGF-I), platelet derived growth factors (PDGF-A and -B), and fibroblast growth factors (FGFs). (Heldin et al., Cell Regulation, 1: 555–566 (1990); Ullrich, et al., Cell, 61: 243–54 (1990)). In each instance, these growth factors exert their action by binding to the extracellular portion of their cognate receptors, which leads to activation of the intrinsic tyrosine kinase present on the cytoplasmic portion of the receptor. Growth factor receptors of endothelial cells are of particular interest due to the possible involvement of growth factors in several important physiological and pathological processes, such as vasculogenesis, angiogenesis, atherosclerosis, and inflammatory diseases. (Folkman, et al. Science, 235:442–447 (1987)). Also, the receptors of several hematopoietic growth factors are tyrosine kinases; these include c-fms, which is the colony stimulating factor 1 receptor, Sherr, et al., Cell, 41: 665–676 (1985), and c-kit, a primitive hematopoietic growth factor receptor reported in Huang, et al., Cell, 63: 225–33 (1990).

The receptor tyrosine kinases have been divided into evolutionary subfamilies based on the characteristic structure of their ectodomains. (Ullrich, et al. Cell, 61: 243–54 (1990)). Such subfamilies include, EGF receptor-like kinase (subclass I) and insulin receptor-like kinase (subclass II), each of which contains repeated homologous cysteine-rich sequences in their extracellular domains. A single cysteine-rich region is also found in the extracellular domains of the eph-like kinases. Hirai, et al., Science, 238: 1717–1720 (1987); Lindberg, et al. Mol. Cell. Biol., 10: 6316–24 (1990); Lhotak, et al., Mol. Cell. Biol. 11: 2496–2502 (1991). PDGF receptors as well as c-fms and c-kit receptor tyrosine kinases may be grouped into subclass III; while the FGF receptors form subclass IV. Typical for the members of both of these subclasses are extracellular folding units stabilized by intrachain disulfide bonds. These so-called immunoglobulin (Ig)-like folds are found in the proteins of the immunoglobulin superfamily which contains a wide variety of other cell surface receptors having either cell-bound or soluble ligands. Williams, et al., Ann. Rev. Immunol., 6: 381–405 (1988).

Receptor tyrosine kinases differ in their specificity and affinity. In general, receptor tyrosine kinases are glycoproteins which consist of (1) an extracellular domain capable of binding the specific growth factor(s); (2) a transmembrane domain which usually is an alpha-helical portion of the protein; (3) a juxtamembrane domain where the receptor may be regulated by, e.g., protein phosphorylation; (4) a tyrosine kinase domain which is the enzymatic component of the receptor; and (5) a carboxyterminal tail which in many receptors is involved in recognition and binding of the substrates for the tyrosine kinase.

Processes such as alternative exon splicing and alternative choice of gene promoter or polyadenylation sites have been reported to be capable of producing several distinct polypeptides from the same gene. These polypeptides may or may not contain the various domains listed above. As a consequence, some extracellular domains may be expressed as separate, secreted proteins and some forms of the receptors may lack the tyrosine kinase domain and contain only the extracellular domain inserted in the plasma membrane via the transmembrane domain plus a short carboxyl terminal tail.

A gene encoding an endothelial cell transmembrane tyrosine kinase, originally identified by RT-PCR as an unknown tyrosine kinase-homologous cDNA fragment from human leukemia cells, was described by Partanen, et al., Proc. Natl. Acad. Sci. USA, 87: 8913–8917 (1990). This gene and its encoded protein are called "TIE" which is an abbreviation for "tyrosine kinase with Ig and EGF homology domains." Partanen, et al. Mol. Cell. Biol. 12: 1698–1707 (1992).

It has been reported that tie mRNA is present in all human fetal and mouse embryonic tissues. Upon inspection, tie message has been localized to the cardiac and vascular endothelial cells. Specifically, tie mRNA has been localized to the endothelia of blood vessels and endocardium of 9.5 to 18.5 day old mouse embryos. Enhanced tie expression was shown during neovascularization associated with developing ovarian follicles and granulation tissue in skin wounds. Korhonen, et al. Blood 80: 2548–2555 (1992). Thus the TIEs have been suggested to play a role in angiogenesis, which is important for developing treatments for solid tumors and several other angiogenesis-dependent diseases such as diabetic retinopathy, psoriasis, atherosclerosis and arthritis.

Two structurally related rat TIE receptor proteins have been reported to be encoded by distinct genes with related profiles of expression. One gene, termed tie-1, is the rat homolog of human tie. Maisonpierre, et al., Oncogene 8: 1631–1637 (1993). The other gene, tie-2, may be the rat homolog of the murine tek gene which, like tie, has been reported to be expressed in the mouse exclusively in endothelial cells and their presumptive progenitors. Dumont, et al. Oncogene 8: 1293–1301 (1993).

The human homolog of tie-2 is described in Ziegler, U.S. Pat. No. 5,447,860 which issued on Sep. 5, 1995 (wherein it is referred to as "ork"), which is incorporated in its entirety herein.

Both genes were found to be widely expressed in endothelial cells of embryonic and postnatal tissues. Significant levels of tie-2 transcripts were also present in other embryonic cell populations, including lens epithelium, heart epicardium and regions of mesenchyme. Maisonpierre, et al., Oncogene 8: 1631–1637 (1993).

The predominant expression of the TIE receptor in vascular endothelia suggests that TIE plays a role in the development and maintenance of the vascular system. This could include roles in endothelial cell determination, proliferation, differentiation and cell migration and patterning into vascular elements. Analyses of mouse embryos deficient in TIE-2 illustrate its importance in angiogenesis, particularly for vascular network formation in endothelial cells. Sato, T. N., et al., Nature 376:70–74 (1995). In the mature vascular system, the TIEs could function in endothelial cell survival, maintenance and response to pathogenic influences.

The TIE receptors are also expressed in primitive hematopoietic stem cells, B cells and a subset of megakaryocytic cells, thus suggesting the role of ligands which bind these receptors in early hematopoiesis, in the differentiation and/or proliferation of B cells, and in the megakaryocytic differentiation pathway. Iwama, et al. Biochem. Biophys. Research Communications 195:301–309 (1993); Hashiyama, et al. Blood 87:93–101 (1996), Batard, et al. Blood 87:2212–2220 (1996).

Applicants previously identified an angiogenic factor, which was originally called TIE-2 ligand-1 (TL1) but is also referred to as angiopoietin-1 (Ang1), that signals through the TIE-2 receptor and is essential for normal vascular development in the mouse. By homology screening applicants have also identified an Ang1 relative, termed TIE-2 ligand-2 (TL2) or angiopoietin-2 (Ang2), that is a naturally occurring antagonist for Ang1 and the TIE2 receptor. For a description of the cloning and sequencing of TL1 (Ang1) and TL2 (Ang2) as well as for methods of making and uses thereof, reference is hereby made to PCT International Publication No. WO 96/11269 published 18 Apr. 1996 and PCT International Publication No. WO 96/31598 published 10 Oct. 1996 both in the name of Regeneron Pharmaceuticals, Inc.; and S. Davis, et al., Cell 87: 1161–1169 (1996) each of which is hereby incorporated by reference. The absence of Ang1 causes severe vascular abnormalities in the developing mouse embryo. C. Suri, et al., Cell 87: 1171–1180 (1996). Ang1 and Ang2 provide for naturally occurring positive and negative regulators of angiogenesis. Positive or negative regulation of TIE2 is likely to result in different outcomes depending on the combination of simultaneously acting angiogenic signals.

SUMMARY OF THE INVENTION

The present invention provides for a composition comprising TIE ligand-3 or TIE ligand-4 substantially free of other proteins. The invention also provides for an isolated nucleic acid molecule encoding TIE ligand-3 and an isolated nucleic acid molecule encoding TIE ligand-4. The isolated nucleic acid may be DNA, cDNA or RNA. The invention also provides for a vector comprising an isolated nucleic acid molecule encoding TIE ligand-3 or TIE ligand-4. The invention further provides for a host-vector system for the production in a suitable host cell of a polypeptide having the biological activity of TIE ligand-3 or TIE ligand-4. The suitable host cell may be bacterial, yeast, insect or mammalian. The invention also provides for a method of producing a polypeptide having the biological activity of TIE ligand-3 or TIE ligand-4 which comprises growing cells of the host-vector system under conditions permitting production of the polypeptide and recovering the polypeptide so produced.

The invention herein described of an isolated nucleic acid molecule encoding TIE ligand-3 or TIE ligand-4 further provides for the development of the ligand, a fragment or derivative thereof, or another molecule which is a receptor agonist or antagonist, as a therapeutic for the treatment of patients suffering from disorders involving cells, tissues or organs which express the TIE receptor. The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The present invention also provides for an antibody which specifically binds TIE ligand-3 or TIE ligand-4. The antibody may be monoclonal or polyclonal. Thus the invention further provides for therapeutic compositions comprising an antibody which specifically binds TIE ligand-3 or TIE ligand-4 and a pharmaceutically acceptable vehicle. The invention also provides for a method of blocking blood vessel growth in a mammal by administering an effective amount of a therapeutic composition comprising an antibody which specifically binds TIE ligand-3 or TIE ligand-4 in a pharmaceutically acceptable vehicle.

The invention further provides for therapeutic compositions comprising TIE ligand-3 or TIE ligand-4 in a pharmaceutically acceptable vehicle. The invention also provides for a method of promoting neovascularization in a patient by administering an effective amount of a therapeutic composition comprising TIE ligand-3 or TIE ligand-4 in a pharmaceutically acceptable vehicle. In one embodiment, the method may be used to promote wound healing. In another embodiment, the method may be used to treat ischemia. In yet another embodiment, TIE ligand-3 or TIE ligand-4 is used, alone or in combination with other hematopoietic factors, to promote the proliferation or differentiation of hematopoietic stem cells, B cells or megakaryocytic cells.

Alternatively, the invention provides that TIE ligand-3 or TIE ligand-4 may be conjugated to a cytotoxic agent and a therapeutic composition prepared therefrom. The invention further provides for a receptorbody which specifically binds TIE ligand-3 or TIE ligand-4. The invention further provides for therapeutic compositions comprising a receptorbody which specifically binds TIE ligand-3 or TIE ligand-4 in a pharmaceutically acceptable vehicle. The invention also provides for a method of blocking blood vessel growth in a mammal by administering an effective amount of a therapeutic composition comprising a receptorbody which specifically binds TIE ligand-3 or TIE ligand-4 in a pharmaceutically acceptable vehicle.

The invention also provides for a TIE receptor antagonist as well as a method of inhibiting TIE ligand-3 or TIE ligand-4 biological activity in a mammal comprising administering to the mammal an effective amount of a TIE antagonist. According to the invention, the antagonist may be the TIE ligand-3 or TIE ligand-4 as described herein, an antibody or other molecule capable of specifically binding TIE ligand-3, TIE ligand-4 or TIE receptor, or a ligandbody comprising the fibrinogen-like domain of TIE ligand-3 or TIE ligand-4.

BRIEF DESCRIPTION OF THE FIGURES

FIG. 1A: embryos treated with EHK-1 RB (rEHK-1 ecto/hIgG1 Fc) were viable and possessed normally developed blood vessels in their surrounding CAM. FIG. 1B: all embryos treated with TIE-2 RB (r TIE-2 ecto/h IgG1 Fc) were dead, diminished in size and were almost completely devoid of surrounding blood vessels.

FIGS. 6A–6B (SEQ ID NOS: 1 and 2)—Nucleotide (SEQ ID NO: 1) and deduced amino acid (single letter code) (SEQ ID NO: 2) sequences of TIE ligand-3. The coding sequence starts at position 47. The fibrinogen-like domain starts at position 929.

FIG. 7 (SEQ ID NOS: 3–8)—Comparison of Amino Acid Sequences of TIE ligand Family Members. mAng3=mTL3= mouse TIE ligand-3 (SEQ ID NO: 3); hAng4=hTL4=human TIE ligand-4 (SEQ ID NO: 4); hAng1=hTL1=human TIE-2 ligand1 (SEQ ID NO: 5); mAng1=mTL1=mouse TIE-2 ligand 1 (SEQ ID NO: 6); mAng2=mTL2=mouse TIE-2 ligand 2 (SEQ ID NO: 7); hAng2=hTL2=human TIE-2 ligand 2 (SEQ ID NO: 8). The underlined regions indicate conserved regions of homology among the family members.

FIGS. 8A–8C—Nucleotide (SEQ ID NO: 9) and deduced amino acid (single letter code) (SEQ ID NO: 10) sequences of TIE ligand-4. Arrow indicates nucleotide position 569.

DETAILED DESCRIPTION OF THE INVENTION

Figure 1A:
FIGS. 1A and 1B—TIE-2 receptorbody (TIE-2 RB) inhibits the development of blood vessels in the embryonic chicken chorioallantoic membrane (CAM). A single piece of resorbable gelatin foam (Gelfoam) soaked with 6 µg of RB was inserted immediately under the CAM of 1-day chick embryos. After 3 further days of incubation, 4 day old embryos and surrounding CAM were removed and examined.

As described in greater detail below, applicants have isolated and identified novel ligands related to the TIE-2 ligands that bind the TIE-2 receptor. The novel ligands, which may be purified from nature, or made recombinantly, are referred to herein as TIE ligand-3 (TL3) and TIE ligand-4 (TL4). The other TIE ligand family members are referred to herein as TIE-2 ligand 1 (TL1) also known as angiopoietin-1 (Ang1), and TIE-2 ligand 2 (TL2) also known as angiopoietin-2 (Ang2). Applicants herein describe a family of TIE ligands and have identified conserved regions of homology among the family members. The novel ligands TL3 and TL4 would therefore be expected to have functions and utilities similar to that of the known ligands TL1 (Ang1) and TL2 (Ang2) in angiogenesis and hematopoiesis.

The present invention comprises the novel ligands and their amino acid sequences, as well as functionally equivalent variants thereof comprising naturally occurring allelic variations, as well as proteins or peptides comprising substitutions, deletions or insertional mutants of the described sequences, which bind TIE receptor and act as agonists or antagonists thereof. Such variants include those in which amino acid residues are substituted for residues within the sequence resulting in a silent change. For example, one or more amino acid residues within the sequence can be substituted by another amino acid(s) of a similar polarity which acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

Also included within the scope of the invention are proteins or fragments or derivatives thereof which exhibit the same or similar biological activity as the TIE ligand-3 or TIE ligand-4 described herein, and derivatives which are differentially modified during or after translation, e.g., by glycosylation, proteolytic cleavage, linkage to an antibody molecule or other cellular ligand, etc. Functionally equivalent molecules also include molecules that contain modifications, including N-terminal modifications, which result from expression in a particular recombinant host, such as, for example, N-terminal methylation which occurs in certain bacterial (e.g. E. coli) expression systems. Functional equivalents also include mutants in which amino acid substitutions are made for cysteine molecules to improve stability of the molecules and to prevent unwanted crosslinking.

The present invention also encompasses the nucleotide sequence that encodes the protein described herein as TIE ligand-3, the nucleotide sequence that encodes the protein described herein as TIE ligand-4, as well as host cells, including yeast, bacteria, viruses, and mammalian cells, which are genetically engineered to produce the protein, by e.g. transfection, transduction, infection, electroporation, or microinjection of nucleic acid encoding the TIE ligand-3 or TIE ligand-4 described herein in a suitable expression vector. The present invention also encompasses introduction of the nucleic acid encoding TIE ligand-3 or TIE ligand-4 through gene therapy techniques such as is described, for example, in Finkel and Epstein FASEB J. 9:843–851 (1995); Guzman, et al. PNAS (USA) 91:10732–10736 (1994).

One skilled in the art will also recognize that the present invention encompasses DNA and RNA sequences that hybridize to a deduced TIE ligand-3 or TIE ligand-4 encoding sequence, under conditions of moderate stringency, as defined in, for example, Sambrook, et al. Molecular Cloning: A Laboratory Manual, 2 ed. Vol. 1, pp. 101–104, Cold Spring Harbor Laboratory Press (1989). Thus, a nucleic acid molecule contemplated by the invention includes one having a sequence deduced from an amino acid sequence of a TIE ligand-3 or TIE ligand-4 prepared as described herein, as well as a molecule having a sequence of nucleic acids that hybridizes to such a nucleic acid sequence, and also a nucleic acid sequence which is degenerate of the above sequences as a result of the genetic code, but which encodes a ligand that binds TIE receptor and which has an amino acid sequence and other primary, secondary and tertiary characteristics that are sufficiently duplicative of the ligand described herein so as to confer on the molecule the same biological activity as the TIE ligand-3 or TIE ligand-4 described herein.

Accordingly, the present invention encompasses an isolated and purified nucleic acid molecule comprising a nucleotide sequence encoding a mammalian TIE ligand-3, wherein the nucleotide sequence is selected from the group consisting of:

(a) the nucleotide sequence comprising the coding region of TIE ligand-3 as set forth in FIGS. 6A–6B (SEQ ID NO: 1);

(b) the nucleotide sequence comprising the coding region of the fibrinogen-like domain of TIE ligand-3 as set forth in FIGS. 6A–6B (SEQ ID NO: 1);

(c) a nucleotide sequence that hybridizes under moderately stringent conditions to the nucleotide sequence of (a) or (b) and which encodes a ligand that binds TIE receptor; and (d) a nucleotide sequence which, but for the degeneracy of the genetic code would hybridize to a nucleotide sequence of (a), (b) or (c), and which encodes a ligand that binds TIE receptor.

The present invention further provides for an isolated and purified TIE ligand-3 encoded by an isolated nucleic acid molecule of the invention. The invention also provides for a vector which comprises an isolated nucleic acid molecule comprising a nucleic acid sequence encoding mammalian TIE ligand-3.

The present invention also encompasses an isolated and purified nucleic acid molecule comprising a nucleotide sequence encoding a human TIE ligand-4, wherein the nucleotide sequence is selected from the group consisting of:

(a) the nucleic acid sequence comprising the coding region of the human TIE ligand-4 contained in the vector designated as hTL-4 deposited on Jul. 2, 1996 (ATCC Accession No. 98095);

(b) the nucleotide sequence comprising the coding region of the fibrinogen-like domain of TIE ligand-4 contained in the vector designated as hTL-4 deposited on Jul. 2, 1996 (ATCC Accession No. 98095);

(c) a nucleotide sequence that hybridizes under moderately stringent conditions to the nucleotide sequence of (a) or (b) and which encodes a ligand that binds TIE receptor; and (d) a nucleotide sequence which, but for the degeneracy of the genetic code would hybridize to a nucleotide sequence of (a), (b) or (c), and which encodes a ligand that binds TIE receptor.

The present invention further encompasses an isolated and purified nucleic acid molecule comprising a nucleotide sequence encoding human TIE ligand-4, wherein the nucleotide sequence is selected from the group consisting of:

(a) the nucleotide sequence comprising the coding region of the human TIE ligand-4 as set forth in FIGS. 8A–8C (SEQ ID NO: 9);

(b) the nucleotide sequence comprising the coding region of the fibrinogen-like domain of human TIE ligand-4 as set forth in FIGS. 8A–8C (SEQ ID NO: 9);

(c) a nucleotide sequence that hybridizes under moderately stringent conditions to the nucleotide sequence of (a) or (b) and which encodes a ligand that binds TIE receptor; and (d) a nucleotide sequence that, as a result of the degeneracy of the genetic code, differs from the nucleotide sequence of (a), (b), or (c) and which encodes a TIE-2 ligand that binds TIE-2 receptor.

The present invention further provides for an isolated and purified TIE ligand-4 encoded by an isolated nucleic acid molecule of the invention. The invention also provides for a vector which comprises an isolated nucleic acid molecule comprising a nucleic acid sequence encoding human TIE ligand-4.

Any of the methods known to one skilled in the art for the insertion of DNA fragments into a vector may be used to construct expression vectors encoding TIE ligand-3 or TIE ligand-4 using appropriate transcriptional/translational control signals and the protein coding sequences. These methods may include in vitro recombinant DNA and synthetic techniques and in vivo recombinations (genetic recombination). Expression of a nucleic acid sequence encoding TIE ligand-3 or TIE ligand-4 or peptide fragments thereof may be regulated by a second nucleic acid sequence which is operably linked to the TIE ligand-3 or TIE ligand-4 encoding sequence such that the TIE ligand-3 or TIE ligand-4 protein or peptide is expressed in a host transformed with the recombinant DNA molecule. For example, expression of TIE ligand-3 or TIE ligand-4 described herein may be controlled by any promoter/enhancer element known in the art. Promoters which may be used to control expression of the ligand include, but are not limited to the long terminal repeat as described in Squinto et al., (Cell 65:1–20 (1991)); the SV40 early promoter region (Bernoist and Chambon, Nature 290:304–310), the CMV promoter, the M-MuLV 5' terminal repeat, the promoter contained in the 3' long terminal repeat of Rous sarcoma virus (Yamamoto, et al., Cell 22:787–797 (1980)), the herpes thymidine kinase promoter (Wagner et al., Proc. Natl. Acad. Sci. U.S.A. 78:144–1445 (1981)), the adenovirus promoter, the regulatory sequences of the metallothionein gene (Brinster et al., Nature 296:39–42 (1982)); prokaryotic expression vectors such as the β-lactamase promoter (Villa-Kamaroff, et al., Proc. Natl. Acad. Sci. U.S.A. 75:3727–3731 (1978)), or the tac promoter (DeBoer, et al., Proc. Natl. Acad. Sci. U.S.A. 80:21–25 (1983)), see also "Useful proteins from recombinant bacteria" in Scientific American, 242:74–94 (1980); promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals; elastase I gene control region which is active in pancreatic acinar cells (Swift et al., Cell 38:639–646 (1984); Ornitz et al., Cold Spring Harbor Symp. Quant. Biol. 50:399–409 (1986); MacDonald, Hepatology 7:425–515 (1987); insulin gene control region which is active in pancreatic beta cells [Hanahan, Nature 315:115–122 (1985)]; immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58); alpha 1-antitrypsin gene control region which is active in the liver (Kelsey et al, 1987, Genes and Devel. 1:161–171), beta-globin gene control region which is active in myeloid cells (Mogram et al., 1985, Nature 315:338–340; Kollias et al., 1986, Cell 46:89–94); myelin basic protein gene control region which is active in oligodendrocytes in the brain (Readhead et al., 1987, Cell 48:703–712); myosin light chain-2 gene control region which is active in skeletal muscle (Shani, 1985, Nature 314:283–286), and gonadotropic releasing hormone gene control region which is active in the hypothalamus (Mason et al., 1986, Science 234:1372–1378). The invention further encompasses the production of antisense compounds which are capable of specifically hybridizing with a sequence of RNA encoding TIE ligand-3 or TIE ligand-4 to modulate its expression. Ecker, U.S. Pat. No. 5,166,195, issued Nov. 24, 1992.

Thus, according to the invention, expression vectors capable of being replicated in a bacterial or eukaryotic host comprising a nucleic acid encoding TIE ligand-3 or TIE ligand-4 as described herein, are used to transfect a host and thereby direct expression of such nucleic acid to produce TIE ligand-3 or TIE ligand-4, which may then be recovered in a biologically active form. As used herein, a biologically active form includes a form capable of binding to TIE receptor and causing a biological response such as a differentiated function or influencing the phenotype of the cell expressing the receptor. Such biologically active forms could, for example, induce phosphorylation of the tyrosine kinase domain of TIE receptor. Alternatively, the biological activity may be an effect as an antagonist to the TIE receptor. In alternative embodiments, the active form of TIE ligand-3 or TIE ligand-4 is one that can recognize TIE receptor and thereby act as a targeting agent for the receptor for use in both diagnostics and therapeutics. In accordance with such embodiments, the active form need not confer upon any TIE expressing cell any change in phenotype.

Expression vectors containing the gene inserts can be identified by four general approaches: (a) DNA-DNA hybridization, (b) presence or absence of "marker" gene functions, (c) expression of inserted sequences and (d) PCR detection. In the first approach, the presence of a foreign gene inserted in an expression vector can be detected by DNA-DNA hybridization using probes comprising sequences that are homologous to an inserted TIE ligand-3 or TIE ligand-4 encoding gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign genes in the vector. For example, if a nucleic acid encoding a TIE ligand-3 or TIE ligand-4 is inserted within the marker gene sequence of the vector, recombinants containing the insert can be identified by the absence of the marker gene function. In the third approach, recombinant expression vectors can be identified by assaying the foreign gene product expressed by the recombinant. Such assays can be based, for example, on the physical or functional properties of a TIE ligand-3 or TIE ligand-4 gene product, for example, by binding of the ligand to TIE receptor or a portion thereof which may be tagged with, for example, a detectable antibody or portion thereof or by binding to antibodies produced against the TIE ligand-3 or TIE ligand-4 protein or a portion thereof. Cells of the present invention may transiently or, preferably, constitutively and permanently express TIE ligand-3 or TIE ligand-4 as described herein. In the fourth approach, DNA nucleotide primers can be prepared corresponding to a tie specific DNA sequence. These primers could then be used to PCR a tie gene fragment. (PCR Protocols: A Guide To Methods and Applications, Edited by Michael A. Innis et al., Academic Press (1990)).

The recombinant ligand may be purified by any technique which allows for the subsequent formation of a stable, biologically active protein.

Preferably, the ligand is secreted into the culture medium from which it is recovered. Alternatively, the ligand may be recovered from cells either as soluble proteins or as inclusion bodies, from which it may be extracted quantitatively by 8M guanidinium hydrochloride and dialysis in accordance with well known methodology. In order to further purify the ligand, affinity chromatography, conventional ion exchange chromatography, hydrophobic interaction chromatography, reverse phase chromatography or gel filtration may be used.

In additional embodiments of the invention, as described in greater detail in the Examples, a recombinant TIE ligand-3 or TIE ligand-4 encoding gene may be used to inactivate or "knock out" the endogenous gene by homologous recombination, and thereby create a TIE ligand-3 or TIE ligand-4 deficient cell, tissue, or animal. For example, and not by way of limitation, the recombinant TIE ligand-3 or TIE ligand-4 encoding gene may be engineered to contain an insertional mutation, for example the neo gene, which would inactivate the native TIE ligand-3 or TIE ligand-4 encoding gene. Such a construct, under the control of a suitable promoter, may be introduced into a cell, such as an embryonic stem cell, by a technique such as transfection, transduction, or injection. Cells containing the construct may then be selected by G418 resistance. Cells which lack an intact TIE ligand-3 or TIE ligand-4 encoding gene may then be identified, e.g. by Southern blotting, PCR detection, Northern blotting or assay of expression. Cells lacking an intact TIE ligand-3 or TIE ligand-4 encoding gene may then be fused to early embryo cells to generate transgenic animals deficient in such ligand. Such an animal may be used to define specific in vivo processes, normally dependent upon the ligand.

The present invention also provides for antibodies to TIE ligand-3 or TIE ligand-4 described herein which are useful for detection of the ligand in, for example, diagnostic applications. For preparation of monoclonal antibodies directed toward TIE ligand-3 or TIE ligand-4, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies to epitopes of TIE ligand-3 or TIE ligand-4 described herein. For the production of antibody, various host animals, including but not limited to rabbits, mice and rats can be immunized by injection with TIE ligand-3 or TIE ligand-4, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected TIE ligand-3 or TIE ligand-4 epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The present invention further encompasses an immunoassay for measuring the amount of TIE ligand-3 or TIE ligand-4 in a biological sample by a) contacting the biological sample with at least one antibody which specifically binds TIE ligand-3 or TIE ligand-4 so that the antibody forms a complex with any TIE ligand-3 or TIE ligand-4 present in the sample; and b) measuring the amount of the complex and thereby measuring the amount of the TIE ligand-3 or TIE ligand-4 in the biological sample.

The invention further encompasses an assay for measuring the amount of TIE receptor in a biological sample by a) contacting the biological sample with at least one ligand of the invention so that the ligand forms a complex with the TIE receptor; and b) measuring the amount of the complex and thereby measuring the amount of the TIE receptor in the biological sample.

The present invention also provides for the utilization of TIE ligand-3 or TIE ligand-4 to support the survival and/or growth and/or migration and/or differentiation of TIE receptor expressing cells. Thus, the ligand may be used as a supplement to support, for example, endothelial cells in culture.

Further, the discovery by applicants of additional ligands for the TIE receptor enables the utilization of assay systems useful for the identification of agonists or antagonists of the TIE receptor. Such assay systems would be useful in identifying molecules capable of promoting or inhibiting angiogenesis. For example, in one embodiment, antagonists of the TIE receptor may be identified as test molecules that are capable of interfering with the interaction of the TIE receptor with biologically active TIE ligand-3 or TIE ligand-4. Such antagonists are identified by their ability to 1) block the binding of biologically active TIE ligand-3 or TIE ligand-4 to the receptor as measured, for example, using BIAcore biosensor technology (BIAcore; Pharmacia Biosensor, Piscataway, N.J.); or 2) block the ability of biologically active TIE ligand-3 or TIE ligand-4 to cause a biological response. Such biological responses include, but are not limited to, phosphorylation of the TIE receptor or downstream components of the TIE signal transduction pathway, or survival, growth or differentiation of TIE receptor bearing cells.

In one embodiment, cells engineered to express the TIE receptor may be dependent for growth on the addition of TIE ligand-3 or TIE ligand-4. Such cells provide useful assay systems for identifying additional agonists of the TIE receptor, or antagonists capable of interfering with the activity of TIE ligand-3 or TIE ligand-4 on such cells. Alternatively, autocrine cells, engineered to be capable of co-expressing both TIE ligand-3 and receptor, or TIE ligand-4 and receptor, may provide useful systems for assaying potential agonists or antagonists.

Therefore, the present invention provides for introduction of a TIE receptor into cells that do not normally express this receptor, thus allowing these cells to exhibit profound and easily distinguishable responses to a ligand which binds this receptor. The type of response elicited depends on the cell utilized, and not the specific receptor introduced into the cell. Appropriate cell lines can be chosen to yield a response of the greatest utility for assaying, as well as discovering, molecules that can act on tyrosine kinase receptors. The molecules may be any type of molecule, including but not limited to peptide and non-peptide molecules, that will act in systems to be described in a receptor specific manner.

One of the more useful systems to be exploited involves the introduction of a TIE receptor (or a chimeric receptor comprising the extracellular domain of another receptor tyrosine kinase such as, for example, trkC and the intracellular domain of a TIE receptor) into a fibroblast cell line (e.g., NIH3T3 cells) thus such a receptor which does not normally mediate proliferative or other responses can, following introduction into fibroblasts, nonetheless be assayed by a variety of well established methods to quantitate effects of fibroblast growth factors (e.g. thymidine incorporation or other types of proliferation assays; see van Zoelen, 1990, "The Use of Biological Assays For Detection Of Polypeptide Growth Factors" in Progress Factor Research, Vol. 2, pp. 131–152; Zhan and M. Goldfarb, 1986, Mol. Cell. Biol., Vol. 6, pp. 3541–3544). These assays have the added advantage that any preparation can be assayed both on the cell line having the introduced receptor as well as the parental cell line lacking the receptor; only specific effects on the cell line with the receptor would be judged as being mediated through the introduced receptor. Such cells may be further engineered to express the TIE ligand-3 or TIE ligand-4, thus creating an autocrine system useful for assaying for molecules that act as antagonists/agonists of this interaction. Thus, the present invention provides for host cells comprising nucleic acid encoding TIE ligand-3 or TIE ligand-4 and nucleic acid encoding TIE receptor.

The TIE receptor/TIE ligand-3 or TIE ligand-4 interaction also provides a useful system for identifying small molecule agonists or antagonists of the TIE receptor. For example, fragments, mutants or derivatives of TIE ligand-3 or TIE ligand-4 may be identified that bind TIE receptor but do not induce any other biological activity. Alternatively, the characterization of TIE ligand-3 or TIE ligand-4 enables the determination of active portions of the molecule. Further, the identification of a ligand enables the determination of the X-ray crystal structure of the receptor/ligand complex, thus enabling identification of the binding site on the receptor. Knowledge of the binding site will provide useful insight into the rational design of novel agonists and antagonists.

The specific binding of a test molecule to TIE receptor may be measured in a number of ways. For example, the actual binding of test molecule to cells expressing TIE may be detected or measured, by detecting or measuring (i) test molecule bound to the surface of intact cells; (ii) test molecule cross-linked to TIE protein in cell lysates; or (iii) test molecule bound to TIE in vitro. The specific interaction between test molecule and TIE may be evaluated by using reagents that demonstrate the unique properties of that interaction.

As a specific, nonlimiting example, the methods of the invention may be used as follows. Consider a case in which the TIE ligand-3 or TIE ligand-4 in a sample is to be measured. Varying dilutions of the sample (the test molecule), in parallel with a negative control (NC) containing no TIE ligand-3 or TIE ligand-4 activity, and a positive control (PC) containing a known amount of TIE ligand-3 or TIE ligand-4, may be exposed to cells that express TIE in the presence of a detectably labeled TIE ligand-3 or TIE ligand-4 (in this example, radioiodinated ligand). The amount of TIE ligand-3 or TIE ligand-4 in the test sample may be evaluated by determining the amount of $^{125}$I-labeled TIE ligand-3 or $^{125}$I-labeled TIE ligand-4 that binds to the controls and in each of the dilutions, and then comparing the sample values to a standard curve. The more TIE ligand-3 or TIE ligand-4 in the sample, the less $^{125}$I-ligand that will bind to TIE.

The amount of $^{125}$I-ligand bound may be determined by measuring the amount of radioactivity per cell, or by cross-linking the TIE ligand-3 or TIE ligand-4 to cell surface proteins using DSS, as described in Meakin and Shooter, 1991, Neuron 6:153–163, and detecting the amount of labeled protein in cell extracts using, for example, SDS polyacrylamide gel electrophoresis, which may reveal a labeled protein having a size corresponding to TIE receptor/TIE ligand-3 or TIE receptor/TIE ligand-4. The specific test molecule/TIE interaction may further be tested by adding to the assays various dilutions of an unlabeled control ligand that does not bind the TIE receptor and therefore should have no substantial effect on the competition between labeled TIE ligand-3 or TIE ligand-4 and test molecule for TIE binding. Alternatively, a molecule known to be able to disrupt TIE receptor/TIE ligand-3 or TIE ligand-4 binding, such as, but not limited to, anti-TIE antibody, or TIE receptorbody as described herein, may be expected to interfere with the competition between $^{125}$I-TIE ligand-3 or $^{125}$I-TIE ligand-4 and test molecule for TIE receptor binding.

Detectably labeled TIE ligand-3 or TIE ligand-4 includes, but is not limited to, TIE ligand-3 or TIE ligand-4 linked covalently or noncovalently to a radioactive substance, a fluorescent substance, a substance that has enzymatic activity, a substance that may serve as a substrate for an enzyme (enzymes and substrates associated with calorimetrically detectable reactions are preferred) or to a substance that can be recognized by an antibody molecule that is preferably a detectably labeled antibody molecule.

Alternatively, the specific binding of test molecule to TIE may be measured by evaluating the secondary biological effects of TIE ligand-3 or TIE ligand-4/TIE receptor binding, including, but not limited to, cell growth and/or differentiation or immediate early gene expression or phosphorylation of TIE. For example, the ability of the test molecule to induce differentiation can be tested in cells that lack tie and in comparable cells that express tie; differentiation in tie-expressing cells but not in comparable cells that lack tie would be indicative of a specific test molecule/TIE interaction. A similar analysis could be performed by detecting immediate early gene (e.g. fos and jun) induction in tie-minus and tie-plus cells, or by detecting phosphorylation of TIE using standard phosphorylation assays known in the art. Such analysis might be useful in identifying agonists or antagonists that do not competitively bind to TIE.

Similarly, the present invention provides for a method of identifying a molecule that has the biological activity of TIE ligand-3 or TIE ligand-4 comprising (i) exposing a cell that expresses tie to a test molecule and (ii) detecting the specific binding of the test molecule to TIE receptor, in which specific binding to TIE positively correlates with TIE-like activity. Specific binding may be detected by either assaying for direct binding or the secondary biological effects of binding, as discussed supra. Such a method may be particularly useful in identifying new members of the TIE ligand family or, in the pharmaceutical industry, in screening a large array of peptide and non-peptide molecules (e.g., peptidomimetics) for TIE associated biological activity. In a preferred, specific, nonlimiting embodiment of the invention, a large grid of culture wells may be prepared that contain, in alternate rows, PC12 (or fibroblasts, see infra) cells that are either tie-minus or engineered to be tie-plus. A variety of test molecules may then be added such that each column of the grid, or a portion thereof, contains a different test molecule. Each well could then be scored for the presence or absence of growth and/or differentiation. An extremely large number of test molecules could be screened for such activity in this manner.

In additional embodiments, the invention provides for methods of detecting or measuring TIE ligand-like activity or identifying a molecule as having such activity comprising (i) exposing a test molecule to a TIE receptor protein in vitro under conditions that permit binding to occur and (ii) detecting binding of the test molecule to the TIE receptor protein, in which binding of test molecule to TIE receptor correlates with TIE ligand-like activity. According to such methods, the TIE receptor may or may not be substantially purified, may be affixed to a solid support (e.g. as an affinity column or as an ELISA assay), or may be incorporated into an artificial membrane. Binding of test molecule to TIE receptor may be evaluated by any method known in the art. In preferred embodiments, the binding of test molecule may be detected or measured by evaluating its ability to compete with detectably labeled known TIE ligands for TIE receptor binding.

The present invention also provides for a method of detecting the ability of a test molecule to function as an antagonist of TIE ligand-like activity comprising detecting the ability of the molecule to inhibit an effect of TIE ligand binding to TIE receptor on a cell that expresses the receptor. Such an antagonist may or may not interfere with TIE receptor/TIE ligand-3 or TIE ligand-4 binding. Effects of TIE ligand-3 or TIE ligand-4 binding to TIE receptor are preferably biological or biochemical effects, including, but not limited to, cell survival or proliferation, cell transformation, immediate early gene induction, or TIE phosphorylation.

The invention further provides for both a method of identifying antibodies or other molecules capable of neutralizing the ligand or blocking binding to the receptor, as well as the molecules identified by the method. By way of nonlimiting example, the method may be performed via an assay which is conceptually similar to an ELISA assay. For example, TIE receptorbody may be bound to a solid support, such as a plastic multiwell plate. As a control, a known amount of TIE ligand-3 or TIE ligand-4 which has been Myc-tagged may then be introduced to the well and any tagged TIE ligand-3 or TIE ligand-4 which binds the receptorbody may then be identified by means of a reporter antibody directed against the Myc-tag. This assay system may then be used to screen test samples for molecules which are capable of i) binding to the tagged ligand or ii) binding to the receptorbody and thereby blocking binding to the receptorbody by the tagged ligand. For example, a test sample containing a putative molecule of interest together with a known amount of tagged ligand may be introduced to the well and the amount of tagged ligand which binds to the receptorbody may be measured. By comparing the amount of bound tagged ligand in the test sample to the amount in the control, samples containing molecules which are capable of blocking ligand binding to the receptor may be identified. The molecules of interest thus identified may be isolated using methods well known to one of skill in the art.

Once a blocker of ligand binding is found, one of skill in the art would know to perform secondary assays to determine whether the blocker is binding to the receptor or to the ligand, as well as assays to determine if the blocker molecule can neutralize the biological activity of the ligand. For example, by using a binding assay which employs BIAcore biosensor technology (or the equivalent), in which either TIE receptorbody or TIE ligand-3 or TIE ligand-4 or ligandbody is covalently attached to a solid support (e.g. carboxymethyl dextran on a gold surface), one of skill in the art would be able to determine if the blocker molecule is binding specifically to the ligand, ligandbody or to the receptorbody. To determine if the blocker molecule can neutralize the biological activity of the ligand, one of skill in the art could perform a phosphorylation assay (see Example 5 in International Publication No. WO 96/31598 published 10 Oct. 1996) or alternatively, a functional bioassay, such as a survival assay, by using primary cultures of, for example, endothelial cells. Alternatively, a blocker molecule which binds to the receptorbody could be an agonist and one of skill in the art would know to how to determine this by performing an appropriate assay for identifying additional agonists of the TIE receptor.

In addition, the invention further contemplates compositions wherein the TIE ligand is the receptor binding domain of the TIE ligand-3 or TIE ligand-4 described herein. For example, TIE-2 ligand 1 contains a "coiled coil" domain and a fibrinogen-like domain. The fibrinogen-like domain of TIE-2 ligand 2 is believed to begin on or around the same amino acid sequence as in ligand 1 (FRDCA). The fibrinogen-like domain of TIE ligand-3 is believed to begin on or around the amino acid sequence which is encoded by nucleotides beginning around position 929 as set forth in FIGS. 6A–6B. Multimerization of the coiled coil domains during production of the ligand hampers purification. As described in Example 7, Applicants have discovered, however, that the fibrinogen-like domain comprises the TIE-2 receptor binding domain. The monomeric forms of the fibrinogen-like domain do not, however, appear to bind the receptor. Studies utilizing myc-tagged fibrinogen-like domain, which has been "clustered" using anti-myc antibodies, do bind the TIE-2 receptor. [Methods of production of "clustered ligands and ligandbodies are described in Davis, et al. Science 266:816–819 (1994)]. Based on these finding, applicants produced "ligandbodies" which comprise the fibrinogen-like domain of the TIE-2 ligands coupled to the Fc domain of IgG ("fFc's"). These ligandbodies, which form dimers, efficiently bind the TIE-2 receptor. Accordingly, the present invention contemplates the production of TIE ligand-3 or TIE ligand-4 ligandbodies which may be used as targeting agents, in diagnostics or in therapeutic applications, such as targeting agents for tumors and/or associated vasculature wherein a TIE antagonist is indicated.

The invention herein further provides for the development of the ligand, a fragment or derivative thereof, or another molecule which is a receptor agonist or antagonist, as a therapeutic for the treatment of patients suffering from disorders involving cells, tissues or organs which express the TIE receptor. Such molecules may be used in a method of treatment of the human or animal body, or in a method of diagnosis.

Because TIE receptor has been identified in association with endothelial cells and, as demonstrated herein, blocking of TIE-2 ligand 1 appears to prevent vascularization, applicants expect that the TIE ligand-3 or TIE ligand-4 may be useful for the induction of vascularization in diseases or disorders where such vascularization is indicated. Such diseases or disorders would include wound healing, ischaemia and diabetes. The ligands may be tested in animal models and used therapeutically as described for other agents, such as vascular endothelial growth factor (VEGF), another endothelial cell-specific factor that is angiogenic. Ferrara, et al. U.S. Pat. No. 5,332,671 issued Jul. 26, 1994. The Ferrara reference, as well as other studies, describe in vitro and in vivo studies that may be used to demonstrate the effect of an angiogenic factor in enhancing blood flow to ischemic myocardium, enhancing wound healing, and in other therapeutic settings wherein neoangiogenesis is desired. [see Sudo, et al.

European Patent Application 0 550 296 A2 published Jul. 7, 1993; Banai, et al. Circulation 89:2183–2189 (1994);

Unger, et al. Am. J. Physiol. 266:H1588–H1595 (1994); Lazarous, et al. Circulation 91:145–153 (1995)]. According to the invention, TIE ligand-3 or TIE ligand-4 may be used alone or in combination with one or more additional pharmaceutically active compounds such as, for example, VEGF or basic fibroblast growth factor (bFGF), as well as cytokines, neurotrophins, etc.

Conversely, antagonists of the TIE receptor, such as receptorbodies as described herein in Examples 2 and 3, and TIE-2 ligand 2 as described in Example 9 in International Publication No. WO 96/31598 published 10 Oct. 1996, would be useful to prevent or attenuate vascularization, thus preventing or attenuating, for example, tumor growth. These agents may be used alone or in combination with other compositions, such as anti-VEGF antibodies, that have been shown to be useful in treating conditions in which the therapeutic intent is to block angiogenesis. Applicants expect that the TIE ligand-3 or TIE ligand-4 described herein may also be used in combination with agents, such as cytokine antagonists such as IL-6 antagonists, that are known to block inflammation.

For example, applicants have determined that TIE ligands are expressed in cells within, or closely associated with, tumors. For example, TIE-2 ligand 2 appears to be tightly associated with tumor endothelial cells. Accordingly, it and other TIE antagonists may also be useful in preventing or attenuating, for example, tumor growth. In addition, TIE ligands or ligandbodies may be useful for the delivery of toxins to a receptor bearing cell. Alternatively, other molecules, such as growth factors, cytokines or nutrients, may be delivered to a TIE receptor bearing cell via TIE ligands or ligandbodies. TIE ligands or ligandbodies such as TIE ligand-3 or TIE ligand-4 may also be used as diagnostic reagents for TIE receptor, to detect the receptor in vivo or in vitro. Where the TIE receptor is associated with a disease state, TIE ligands or ligandbodies such as TIE ligand-3 or TIE ligand-4 may be useful as diagnostic reagents for detecting the disease by, for example, tissue staining or whole body imaging. Such reagents include radioisotopes, flurochromes, dyes, enzymes and biotin. Such diagnostics or targeting agents may be prepared as described in Alitalo, et al. WO 95/26364 published Oct. 5, 1995 and Burrows, F. and P. Thorpe, PNAS (USA) 90:8996–9000 (1993) which is incorporated herein in its entirety.

In other embodiments, the TIE ligands, such as TIE ligand-3 or TIE ligand-4, described herein are used as hematopoietic factors. A variety of hematopoietic factors and their receptors are involved in the proliferation and/or differentiation and/or migration of the various cells types contained within blood. Because the TIE receptors are expressed in early hematopoietic cells, the TIE ligands are expected to play a comparable role in the proliferation or differentiation or migration of these cells. Thus, for example, TIE containing compositions may be prepared, assayed, examined in in vitro and in vivo biological systems and used therapeutically as described in any of the following: Sousa, U.S. Pat. No. 4,810,643, Lee, et al., Proc. Natl. Acad. Sci. USA 82:4360–4364 (1985) Wong, et al. Science, 228:810–814 (1985); Yokota, et al. Proc. Natl. Acad. Sci (USA) 81:1070 (1984); Bosselman, et al. WO 9105795 published May 2, 1991 entitled "Stem Cell Factor" and Kirkness, et al. WO 95/19985 published Jul. 27, 1995 entitled "Haemopoietic Maturation Factor". Accordingly, TIE ligand-3 or TIE ligand-4 may be used to diagnose or treat conditions in which normal hematopoiesis is suppressed, including, but not limited to anemia, thrombocytopenia, leukopenia and granulocytopenia. In a preferred embodiment, TIE ligand-3 or TIE ligand-4 may be used to stimulate differentiation of blood cell precursors in situations where a patient has a disease, such as acquired immune deficiency syndrome (AIDS) which has caused a reduction in normal blood cell levels, or in clinical settings in which enhancement of hematopoietic populations is desired, such as in conjunction with bone marrow transplant, or in the treatment of aplasia or myelosuppression caused by radiation, chemical treatment or chemotherapy.

The TIE ligand-3 or TIE ligand-4 of the present invention may be used alone, or in combination with another pharmaceutically active agent such as, for example, ctyokines, neurotrophins, interleukins, etc. In a preferred embodiment, the ligand may be used in conjunction with any of a number of the above referenced factors which are known to induce stem cell or other hematopoietic precursor proliferation, or factors acting on later cells in the hematopoietic pathway, including, but not limited to, hemopoietic maturation factor, thrombopoietin, stem cell factor, erythropoietin, G-CSF, GM-CSF, etc.

In an alternative embodiment, TIE receptor antagonists are used to diagnose or treat patients in which the desired result is inhibition of a hematopoietic pathway, such as for the treatment of myeloproliferative or other proliferative disorders of blood forming organs such as thrombocythemias, polycythemias and leukemias. In such embodiments, treatment may comprise use of a therapeutically effective amount of the TIE ligand-3 or TIE ligand-4, TIE antibody, TIE receptorbody, a conjugate of TIE ligand-3 or TIE ligand-4, or a ligandbody or fFC as described herein.

The present invention also provides for pharmaceutical compositions comprising the TIE ligand-3 or TIE ligand-4 or ligandbodies described herein, peptide fragments thereof, or derivatives in a pharmacologically acceptable vehicle. The TIE ligand-3 or TIE ligand-4 proteins, peptide fragments, or derivatives may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

The present invention also provides for an antibody which specifically binds such a therapeutic molecule. The antibody may be monoclonal or polyclonal. The invention also provides for a method of using such a monoclonal or polyclonal antibody to measure the amount of the therapeutic molecule in a sample taken from a patient for purposes of monitoring the course of therapy.

The invention further provides for a therapeutic composition comprising a TIE ligand-3 or TIE ligand-4 or ligandbody and a cytotoxic agent conjugated thereto. In one embodiment, the cytotoxic agent may be a radioisotope or toxin.

The invention also provides for an antibody which specifically binds a TIE ligand-3 or TIE ligand-4. The antibody may be monoclonal or polyclonal.

The invention further provides for a method of purifying TIE ligand-3 or TIE ligand-4 comprising:
 a) coupling at least one TIE binding substrate to a solid matrix;
 b) incubating the substrate of a) with a cell lysate so that the substrate forms a complex with any TIE ligand-3 or TIE ligand-4 in the cell lysate;
 c) washing the solid matrix; and
 d) eluting the TIE ligand-3 or TIE ligand-4 from the coupled substrate.

The substrate may be any substance that specifically binds the TIE ligand-3 or TIE ligand-4. In one embodiment, the substrate is selected from the group consisting of anti-TIE ligand-3 or anti-TIE ligand-4 antibody, TIE receptor and TIE receptorbody. The invention further provides for a receptorbody which specifically binds TIE ligand-3 or TIE ligand-4, as well as a therapeutic composition comprising the receptorbody in a pharmaceutically acceptable vehicle, and a method of blocking blood vessel growth in a human comprising administering an effective amount of the therapeutic composition.

The invention also provides for a therapeutic composition comprising TIE ligand-3 or TIE ligand-4 or ligandbody in a pharmaceutically acceptable vehicle, as well as a method of promoting neovascularization in a patient comprising administering to the patient an effective amount of the therapeutic composition.

In addition, the present invention provides for a method for identifying a cell which expresses TIE receptor which comprises contacting a cell with a detectably labeled TIE ligand-3 or TIE ligand-4 or ligandbody, under conditions permitting binding of the detectably labeled ligand to the TIE receptor and determining whether the detectably labeled ligand is bound to the TIE receptor, thereby identifying the cell as one which expresses TIE receptor. The present invention also provides for a therapeutic composition comprising a TIE TIE ligand-3 or ligand-4 or ligandbody and a cytotoxic agent conjugated thereto. The cytotoxic agent may be a radioisotope or toxin.

The invention also provides a method of detecting expression of TIE ligand-3 or TIE ligand-4 by a cell which comprises obtaining mRNA from the cell, contacting the mRNA so obtained with a labeled nucleic acid molecule encoding TIE ligand-3 or TIE ligand-4, under hybridizing conditions, determining the presence of mRNA hybridized to the labeled molecule, and thereby detecting the expression of the TIE ligand-3 or TIE ligand-4 in the cell.

The invention further provides a method of detecting expression of TIE ligand-3 or TIE ligand-4 in tissue sections which comprises contacting the tissue sections with a labeled nucleic acid molecule encoding a TIE ligand-3 or TIE ligand-4, under hybridizing conditions, determining the presence of mRNA hybridized to the labelled molecule, and thereby detecting the expression of TIE ligand-3 or TIE ligand-4 in tissue sections.

EXAMPLE 1

Identification of the ABAE Cell Line as Reporter Cells for the TIE-2 Receptor

Adult BAE cells are registered in the European Cell Culture Repository, under ECACC#92010601. (See PNAS 75:2621 (1978)). Northern (RNA) analyses revealed moderate levels of tie-2 transcripts in the ABAE (Adult Bovine Arterial Endothelial) cell line, consistent with in situ hybridization results that demonstrated almost exclusive localization of tie-2 RNAs to vascular endothelial cells. We therefore examined ABAE cell lysates for the presence of TIE-2 protein, as well as the extent to which this TIE-2 protein is tyrosine-phosphorylated under normal versus serum-deprived growth conditions. ABAE cell lysates were harvested and subjected to immunoprecipitation, followed by Western blot analyses of immunoprecipitated proteins with TIE-2 specific and phosphotyrosine-specific antisera. Omission or inclusion of TIE-2 peptides as specific blocking molecules during TIE-2 immunoprecipitation allowed unambiguous identification of TIE-2 as a moderately detectable protein of ~150 kD whose steady-state phosphotyrosine levels diminish to near undetectable levels by prior serum-starvation of the cells.

Culture of ABAE cells and harvest of cell lysates was done as follows. Low-passage-number ABAE cells were plated as a monolayer at a density of $2 \times 10^6$ cells/150 mm plastic petri plate (Falcon) and cultured in Dulbecco's modified Eagle's medium (DMEM) containing 10% bovine calf serum (10% BCS), 2 mM L-glutamine (Q) and 1% each of penicillin and streptomycin (P-S) in an atmosphere of 5% $CO_2$. Prior to harvest of cell lysates, cells were serum-starved for 24 hours in DMEM/Q/P-S, followed by aspiration of the medium and rinsing of the plates with ice-cold phosphate buffered saline (PBS) supplemented with sodium orthovanadate, sodium fluoride and sodium benzamidine. Cells were lysed in a small volume of this rinse buffer that had been supplemented with 1% NP40 detergent and the protease inhibitors PMSF and aprotinin. Insoluble debris was removed from the cell lysates by centrifugation at $14,000 \times G$ for 10 minutes, at 4° C. and the supernatants were subjected to immunoprecipitation with antisera specific for TIE-2 receptor, with or without the presence of blocking peptides added to ~20 µg/ml lysate. Immunoprecipitated proteins were resolved by PAGE (7.5% Laemmli gel), and then electro-transferred to PVDF membrane and incubated either with various TIE-2- or phosphotyrosine-specific antisera. TIE-2 protein was visualized by incubation of the membrane with HRP-linked secondary antisera followed by treatment with ECL reagent (Amersham).

EXAMPLE 2

Cloning and Expression of TIE-2 Receptorbody for Affinity-based Study of TIE-2 Ligand Interactions An expression construct was created that would yield a secreted protein consisting of the entire extracellular portion of the rat TIE-2 receptor fused to the human immunoglobulin gamma-1 constant region (IgG1 Fc). This fusion protein is called a TIE-2 "receptorbody" (RB), and would be normally expected to exist as a dimer in solution based on formation of disulfide linkages between individual IgG1 Fc tails. The Fc portion of the TIE-2 RB was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding the full-length TIE-2 receptor and from the human IgG1 Fc plasmid were ligated on either side of a short PCR-derived fragment that was designed so as to fuse, in-frame, the TIE-2 and human IgG1 Fc protein-coding sequences. Thus, the resulting TIE-2 ectodomain-Fc fusion protein precisely substituted the IgG1 Fc in place of the region spanning the TIE-2 transmembrane and cytoplasmic domains. An alternative method of preparing RBs is described in Goodwin, et. al. Cell 73:447–456 (1993).

Milligram quantities of TIE-2 RB were obtained by cloning the TIE-2 RB DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1-4 may be used. DNA encoding the TIE-2 RB was cloned as an EcoRI-NotI fragment into the baculovirus transfer plasmid pVL1393.

Plasmid DNA purified by cesium chloride density gradient centrifugation was recombined into viral DNA by mixing 3 μg of plasmid DNA with 0.5 μg of Baculo-Gold DNA (Pharminigen), followed by introduction into liposomes using 30 μg Lipofectin (GIBCO-BRL). DNA-liposome mixtures were added to SF-21AE cells ($2 \times 10^6$ cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, *Baculovirus Expression Vectors—A Laboratory Manual*. 1992, New York: W. H. Freeman) except that the agarose overlay contained 125 μg/mL X-gal (5-bromo-4-chloro-3-indolyl-β-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 μg/mL MTT (3-[4,5-dimethylthiazol-2-yl]2,5,-diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTIE-2 receptorbody) were produced.

SF-21AE cells were cultured in serum free medium (SF-900 II, Gibco BRL) containing 1×antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~$2 \times 10^6$ cells/mL), concentrated by centrifugation, and infected with 5 plaque forming units of vTIE-2 receptorbody per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTIE-2 receptorbody-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 μm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TIE-2 receptorbody were pooled and dialyzed versus PBS.

EXAMPLE 3

Demonstration that TIE-2 has a Critical Role in Development of the Vasculature

Insight into the function of TIE-2 was gained by introduction of "excess" soluble TIE-2 receptorbody (TIE-2 RB) into a developing system. The potential ability of TIE-2 RB to bind, and thereby neutralize, available TIE-2 ligand could result in an observable disruption of normal vascular development and characterization of the ligand. To examine whether TIE-2 RB could be used to disrupt vascular development in early chick embryos, small pieces of a biologically resorbable foam were soaked with TIE-2 RB and inserted immediately beneath the chorioallantoic membrane at positions just lateral to the primitive embryo.

Early chicken embryos develop atop the yolk from a small disk of cells that is covered by the chorioallantoic membrane (CAM). The endothelial cells that will come to line the vasculature in the embryo arise from both extra- and intra-embryonic cell sources. Extra-embryonically-derived endothelial cells, which provide the major source of endothelial cells in the embryo, originate from accretions of mesenchyme that are situated laterally around the embryo-proper, just underneath the CAM. As these mesenchyme cells mature, they give rise to a common progenitor of both the endothelial and hematopoietic cell lineages, termed the hemangioblast. In turn, the hemangioblast gives rise to a mixed population of angioblasts (the endothelial cell progenitor) and hematoblasts (the pluripotential hematopoietic precursor). Formation of rudiments of the circulatory system begins when endothelial cell progeny segregate to form a one-cell-thick vesicle that surrounds the primitive blood cells. Proliferation and migration of these cellular components eventually produces a vast network of blood-filled microvessels under the CAM that will ultimately invade the embryo to join with limited, intra-embryonically-derived vascular elements.

Figure 1B:

Newly fertilized chicken eggs obtained from Spafas, Inc. (Boston, Mass.) were incubated at 99.5° F., 55% relative humidity. At about 24 hrs. of development, the egg shell was wiped down with 70% ethanol and a dentist's drill was used to make a 1.5 cm. hole in the blunt apex of each egg. The shell membrane was removed to reveal an air space directly above the embryo. Small rectangular pieces of sterile Gelfoam (Upjohn) were cut with a scalpel and soaked in equal concentrations of either TIE-2- or EHK-1 receptorbody. EHK-1 receptorbody was made as set forth in Example 2 using the EHK-1 extracellular domain instead of the TIE-2 extracellular domain (Maisonpierre et al., Oncogene 8:3277–3288 (1993). Each Gelfoam piece absorbed approximately 6 μg of protein in 30 μl. Sterile watchmakers forceps were used to make a small tear in the CAM at a position several millimeters lateral to the primitive embryo. The majority of the piece of RB-soaked Gelfoam was inserted under the CAM and the egg shell was sealed over with a piece of adhesive tape. Other similarly-staged eggs were treated in parallel with RB of the unrelated, neuronally expressed receptor tyrosine kinase, EHK-1 (Maisonpierre et al., Oncogene 8:3277–3288 (1993). Development was allowed to proceed for 4 days and then the embryos were examined by visual inspection. Embryos were removed by carefully breaking the shells in dishes of warmed PBS and carefully cutting away the embryo with surrounding CAM. Of 12 eggs treated with each RB, 6 TIE-2 RB and 5 EHK-1 RB treated embryos had developed beyond the stage observed at the start of the experiment. A dramatic difference was seen between these developed embryos, as shown in FIGS. 1A and 1B. Those treated with EHK-1 RB appeared to have developed relatively normally. Four out of five EHK-1 embryos were viable as judged by the presence of a beating heart. Furthermore, the extra-embryonic vasculature, which is visually obvious due to the presence of red blood cells, was profuse and extended several centimeters laterally under the CAM. By contrast, those treated with TIE-2 RB were severely stunted, ranging from 2–5 mm. in diameter, as compared with more than 10 mm in diameter for the EHK-1 RB embryos. All of the TIE-2 RB treated embryos were dead and their CAMs were devoid of blood vessels. The ability of TIE-2 RB to block vascular development in the chicken demonstrates that TIE-2 ligand is necessary for development of the vasculature.

EXAMPLE 4

Construction of TIE-2 Ligandbodies

An expression construct was created that would yield a secreted protein consisting of the entire coding sequence of human TIE-2 ligand 1 (TL1) or TIE-2 ligand 2 (TL2) fused to the human immunoglobulin gamma-1 constant region (IgG1 Fc). These fusion proteins are called TIE-2 "ligandbodies" (TL1-Fc or TL2-Fc). The Fc portion of TL1-Fc and TL2-Fc was prepared as follows. A DNA fragment encoding the Fc portion of human IgG1 that spans from the hinge region to the carboxy-terminus of the protein, was amplified from human placental cDNA by PCR with oligonucleotides corresponding to the published sequence of human IgG1; the resulting DNA fragment was cloned in a plasmid vector. Appropriate DNA restriction fragments from a plasmid encoding full-length TL1 or TL2 and from the human IgG1 Fc plasmid were ligated on either side of a short PCR-derived fragment that was designed so as to fuse, in-frame, TL1 or TL2 with human IgG1 Fc protein-coding sequences.

Milligram quantities of TL2-Fc were obtained by cloning the TL2-Fc DNA fragment into the pVL1393 baculovirus vector and subsequently infecting the *Spodoptera frugiperda* SF-21AE insect cell line. Alternatively, the cell line SF-9 (ATCC Accession No. CRL-1711) or the cell line BTI-TN-5b1–4 may be used. DNA encoding the TL2-Fc was cloned as an EcoRI-NotI fragment into the baculovirus transfer plasmid pVL1393.

Plasmid DNA was recombined into viral DNA by mixing 3 µg of plasmid DNA with 0.5 µg of Baculo-Gold DNA (Pharminigen), followed by introduction into liposomes using 30 µg Lipofectin (GIBCO-BRL). DNA-liposome mixtures were added to SF-21AE cells (2×106 cells/60 mm dish) in TMN-FH medium (Modified Grace's Insect Cell Medium (GIBCO-BRL) for 5 hours at 27° C., followed by incubation at 27° C. for 5 days in TMN-FH medium supplemented with 5% fetal calf serum. Tissue culture medium was harvested for plaque purification of recombinant viruses, which was carried out using methods previously described (O'Reilly, D. R., L. K. Miller, and V. A. Luckow, Baculovirus Expression Vectors—A Laboratory Manual. 1992, New York: W. H. Freeman) except that the agarose overlay contained 125 mg/mL X-gal (5-bromo-4-chloro-3-indolyl-b-D-galactopyranoside; GIBCO-BRL). After 5 days of incubation at 27° C., non-recombinant plaques were scored by positive chromogenic reaction to the X-gal substrate, and their positions marked. Recombinant plaques were then visualized by addition of a second overlay containing 100 mg/mL MTT (3-[4,5-dimethylthiazol-2-yl] 2,5,diphenyltetrazolium bromide; Sigma). Putative recombinant virus plaques were picked by plug aspiration, and purified by multiple rounds of plaque isolation to assure homogeneity. Virus stocks were generated by serial, low-multiplicity passage of plaque-purified virus. Low passage stocks of one virus clone (vTL2-Fc Clone #7) were produced.

SF-21AE cells were cultured in serum-free medium (SF-900 II, Gibco BRL) containing 1×antibiotic/antimycotic solution (Gibco BRL) and 25 mg/L Gentamycin (Gibco BRL). Pluronic F-68 was added as a surfactant to a final concentration of 1 g/L. Cultures (4 L) were raised in a bioreactor (Artisan Cell Station System) for at least three days prior to infection. Cells were grown at 27° C., with gassing to 50% dissolved oxygen, at a gas flow rate of 80 mL/min (aeration at a sparge ring). Agitation was by means of a marine impeller at a rate of 100 rpm. Cells were harvested in mid-logarithmic growth phase (~2×10 6 cells/mL), concentrated by centrifugation, and infected with 5 plaque forming units of vTL2-Fc per cell. Cells and inoculum were brought to 400 mL with fresh medium, and virus was adsorbed for 2 hours at 27° C. in a spinner flask. The culture was then resuspended in a final volume of 8 L with fresh serum-free medium, and the cells incubated in the bioreactor using the previously described conditions.

Culture medium from vTL2-Fc-infected SF21AE cells were collected by centrifugation (500×g, 10 minutes) at 72 hours post-infection. Cell supernatants were brought to pH 8 with NaOH. EDTA was added to a final concentration of 10 mM and the supernatant pH was readjusted to 8. Supernatants were filtered (0.45 µm, Millipore) and loaded on a protein A column (protein A sepharose 4 fast flow or HiTrap protein A, both from Pharmacia). The column was washed with PBS containing 0.5 M NaCl until the absorbance at 280 nm decreased to baseline. The column was washed in PBS and eluted with 0.5 M acetic acid. Column fractions were immediately neutralized by eluting into tubes containing 1 M Tris pH 9. The peak fractions containing the TL2-Fc were pooled and dialyzed versus PBS.

EXAMPLE 5 the TIE Receptor/Ligand System in Angiogenesis

Although the TIE-2/TIE ligand system appears to play an important role in endothelial cell biology, it has not been shown to play a significant, active role in the early to intermediate stages of vascularization (e.g. angioblast or endothelial cell proliferation and migration, tubule formation, and other early stage events in vascular modeling). In contrast to the receptors and factors known to mediate these aspects of vascular development, the temporally late pattern of expression of TIE-2 and TL1 in the course of vascularization suggests that this system plays a distinct role in the latter stages vascular development, including the structural and functional differentiation and stabilization of new blood vessels. The pattern of expression of TIE-2/TL1 also is consistent with a continuing role in the maintenance of the structural integrity and/or physiological characteristics of an established vasculature.

Figure 2:
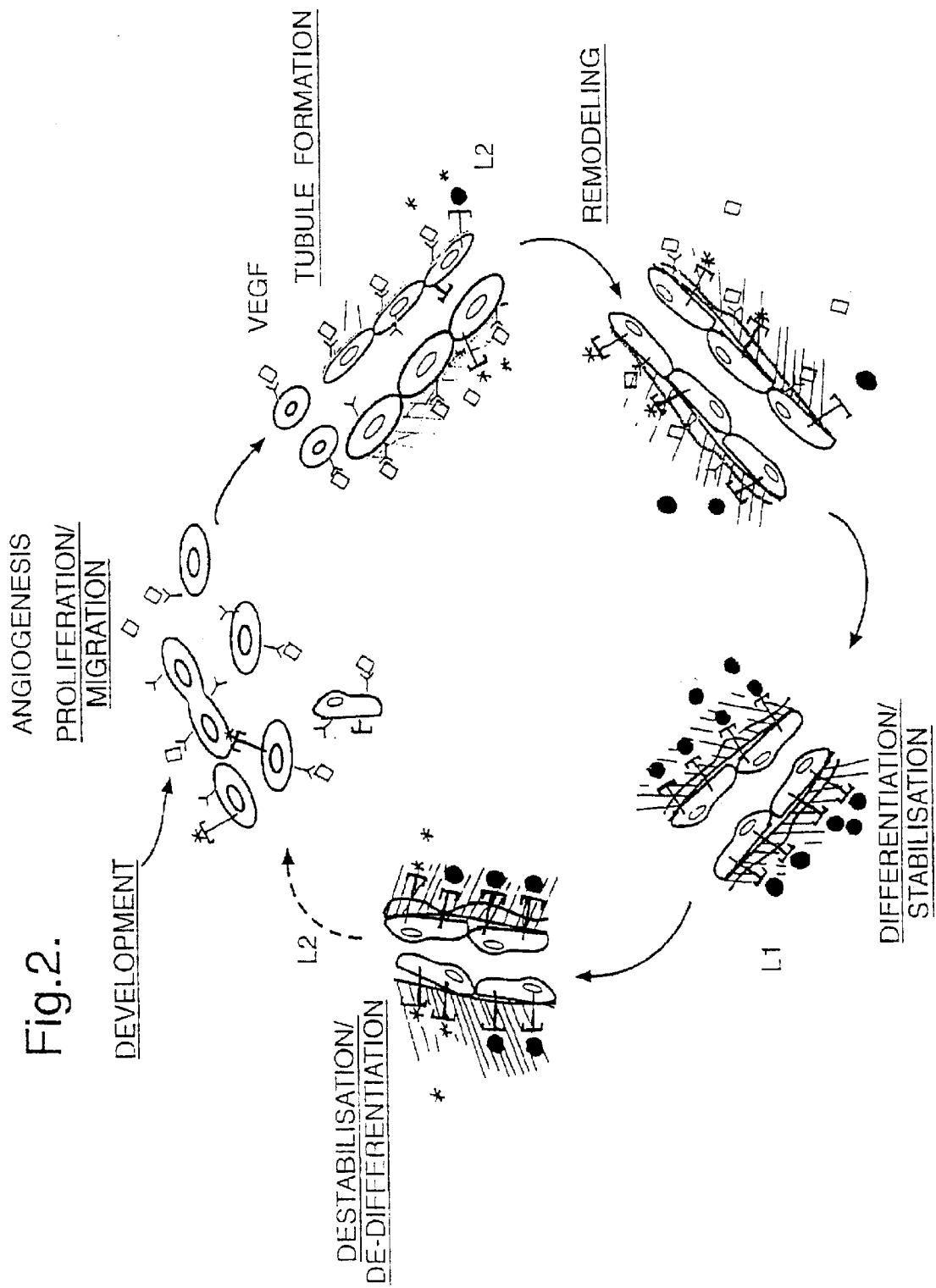
FIG. 2—A schematic representation of the hypothesized role of the TIE-2/TIE ligands in angiogenesis. TL1 is represented by (•), TL2 is represented by (*), TIE-2 is represented by (T), VEGF is represented by ([ ]), and flk-1 (a VEGF receptor) is represented by (Y).

TIE Ligand 2 (TL2) appears to be a competitive inhibitor of TL1. The spatiotemporal characteristics of TL2 expression suggest that this single inhibitory molecule may play multiple, context-dependent roles essential to appropriate vascular development or remodeling (e.g. de-stabilization/de-differentiation of mature endothelial cells allowing the formation of new vessels from existing vasculature, inhibition of inappropriate blood vessel formation, and regression/involution of mature blood vessels). FIG. 2 is a schematic representation of the hypothesized role of the TIE-2/TIE ligands in angiogenesis. In this figure TL1 is represented by (•), TL2 is represented by (*), TIE-2 is represented by (T), VEGF is represented by ([ ]), and flk-1 (a VEGF receptor) is represented by (Y).

EXAMPLE 6

Construction and Characterization of the CYS⁻ TL1 Mutant

Figure 3:
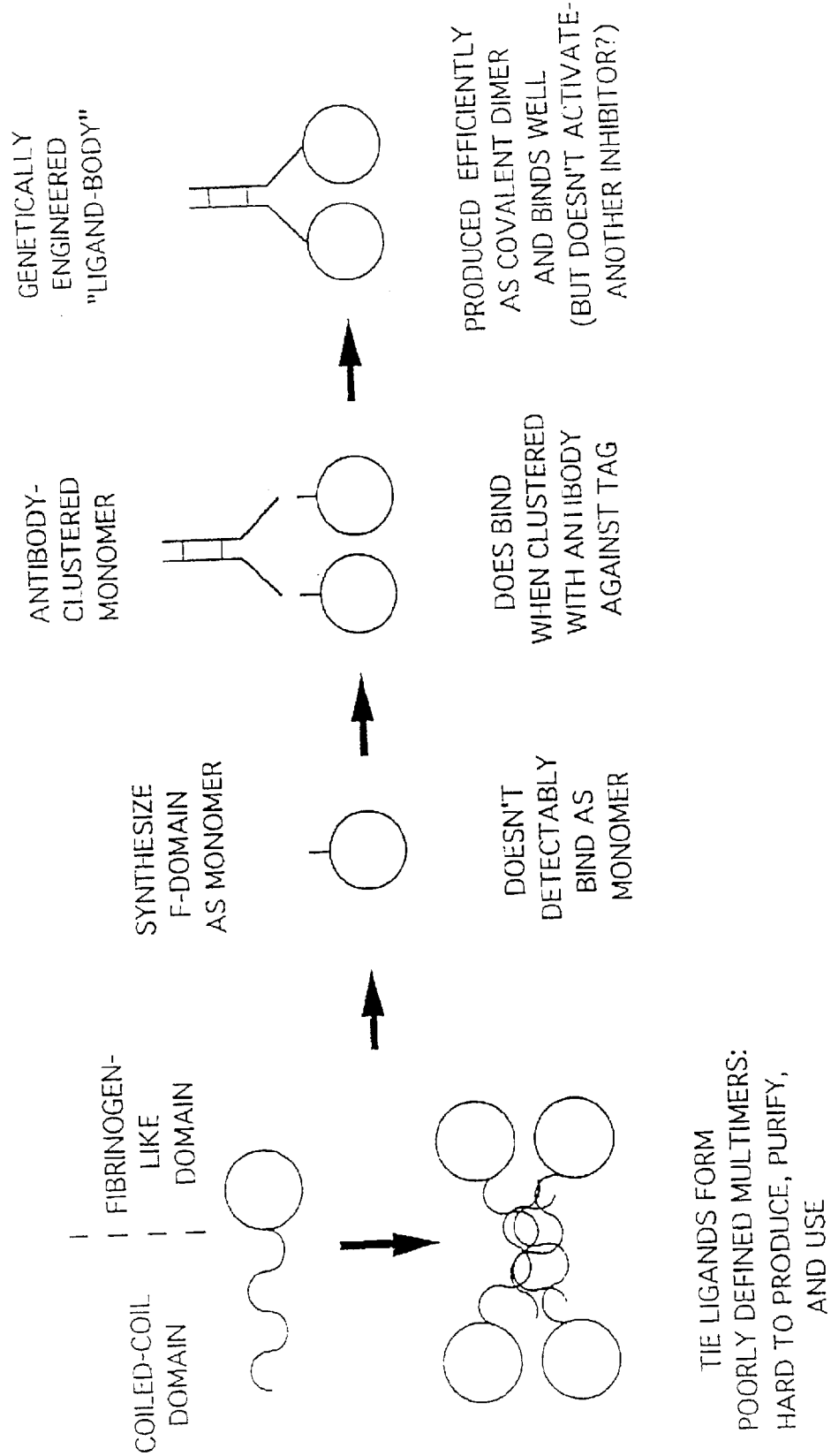
FIG. 3—Diagrammatic representation of the TIE-2 ligands, showing the "coiled coil" and fibrinogen-like domains and the engineering of multimers of the fibrinogen-like domains using antibodies to myc-tags as well as Fc tagging.

The TIE-2 ligands have two major structural domains, one described as a "coiled-coil" domain comprising the approximate C-terminal third of the protein and the other a "fibrinogen-like" domain comprising the approximate N-terminal two-thirds of the protein. Although the TIE-2 ligands, designated TL1 and TL2, share similar structural homology, they exhibit different physical and biological properties. Under non-reducing electrophoretic conditions, both proteins exhibit covalent, multimeric structures, with TL1 existing primarily as a trimer and TL2 existing primarily as a dimer. FIG. 3 is a schematic representation of how the TIE-2 ligands may be interacting to form multimers. In terms of biological activity, TL1 has been shown to be an agonist of the TIE-2 receptor, as demonstrated by induction of phosphorylation in TIE-2 expressing cells. TL2, on the other hand, appears to be a competitive inhibitor of TL1. Investigations into what factors might be contributing to the different physical and biological properties of the two molecules revealed the presence of a cysteine residue (CYS265) preceding the fibrinogen-like domain in TL1 but absent in TL2. This CYS265 residue in TL1 is encoded by TGC and is located at about nucleotides 1102–1104 at the approximate junction between the coiled-coil and fibrinogen-like domains. Because cysteine residues are generally involved in disulfide bond formation, the presence of which can contribute to both the tertiary structure and biological properties of a molecule, it was thought that perhaps the presence of the CYS265 in TL1 might be at least partially responsible for the different properties of the two molecules. To test this hypothesis, an expression plasmid was constructed which contained a mutation in TL1 in which the CYS was replaced with an amino acid which does not form disulfide bonds. In addition to this TL1/CYS⁻ mutant, a second expression plasmid was constructed which mutated the corresponding position in TL2 so that this residue was now a cysteine. Both non-mutated and mutated expression plasmids of TL1 and TL2 were transiently transfected into COS cells. Cell supernatants containing the recombinant proteins were harvested and samples subjected to both reducing and non-reducing SDS/PAGE electrophoresis and subsequent western blotting. Western blots of both non-mutated and mutated TL1 and TL2 proteins revealed that the TL1/CYS⁻ mutant behaves more TL2-like in that it runs as a dimer and that the TL2/CYS+ mutant behaves more TL1-like in that it is able to form a trimer as well as higher-order multimers. Interestingly, when the two mutant proteins were tested for their ability to induce phosphorylation in TIE-2 expressing cells, the TL1/CYS⁻ mutant was able to activate the TIE-2 receptor, whereas the TL2/CYS+ mutant did not gain any activating activity.

EXAMPLE 7

Construction and Characterization of Fibrinogen-like Domain Only Mutants

In order to test whether the fibrinogen-like domain (F-domain) of the TIE-2 ligands contained TIE-2 activating activity, expression plasmids were constructed which deleted the coiled-coil domain, leaving only that portion of the DNA sequence encoding the F-domain (beginning at about nucleotide 1159, amino acid residue ARG284). This mutant construct was transiently transfected into COS cells. The supernatant containing the recombinant protein was harvested. The TL1/F-domain mutant was tested for it's ability to bind the TIE-2 receptor. The results showed that, as a monomer, the TL1/F-domain mutant was not able to bind TIE-2 at a detectable level. However, when the TL1/F-domain monomer was myc-tagged and subsequently clustered with an antibody directed against the myc tag, it did exhibit detectable binding to TIE-2. However, the antibody-clustered TL1/F-domain mutant was not able to induce phosphorylation in a TIE-2 expressing cell line. FIG. 3 shows a schematic representation of the F-domain construct and its binding ability plus and minus antibody clustering.

EXAMPLE 8

A Receptorbody Binding Assay and a Ligand Binding and Competition Assay

Figure 4:
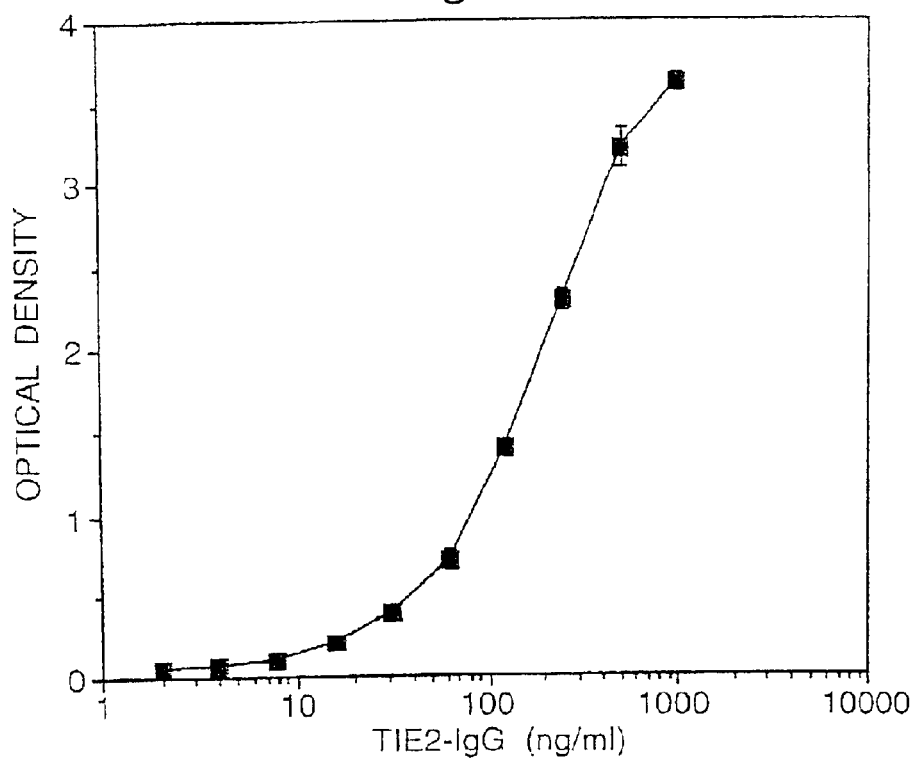
FIG. 4—A typical curve of TIE-2-IgG binding to immobilized TL1 in a quantitative cell-free binding assay.
Figure 5:
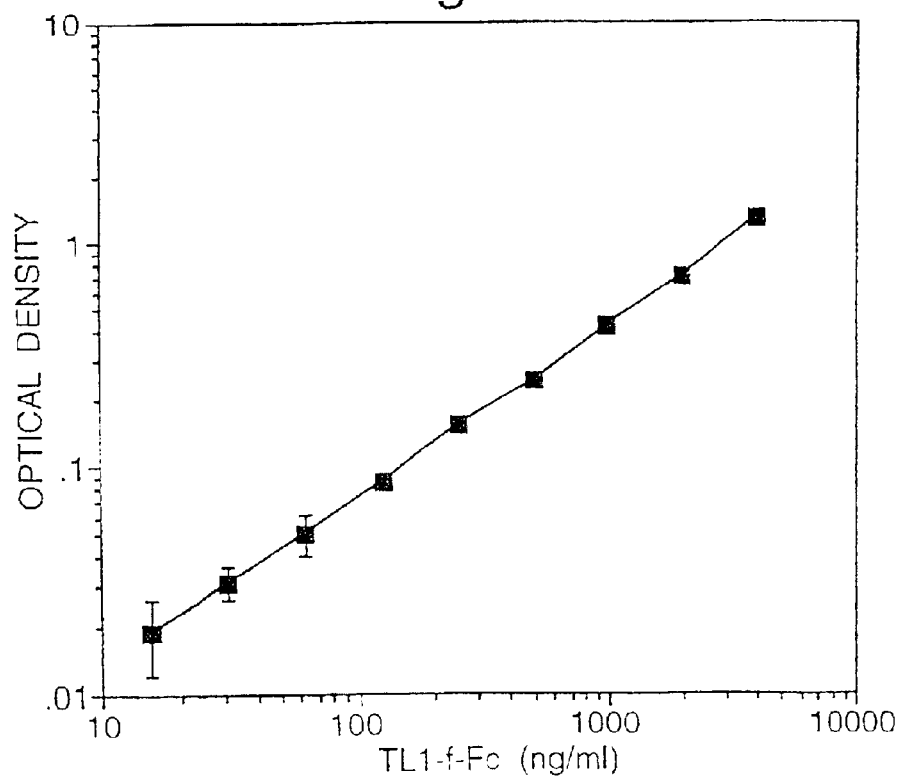
FIG. 5—A typical curve showing TIE-2 ligand 1 ligandbody comprising the fibrinogen-like domain of the ligand bound to the Fc domain of IgG (TL1-fFc) binding to immobilized TIE-2 ectodomain in a quantitative cell-free binding assay.

A quantitative cell-free binding assay with two alternate formats has been developed for detecting either TIE-2 receptorbody binding or ligand binding and competition. In the receptorbody binding version of the assay, TIE-2 ligands (purified or partially purified; either TL1 or TL2) are coated onto an ELISA plate. Receptorbody at varying concentrations is then added, which binds to the immobilized ligand in a dose-dependent manner. At the end of 2 hours, excess receptorbody is washed away, then the amount bound to the plate is reported using a specific antihuman Fc antibody which is alkaline phosphatase tagged. Excess reporter antibody is washed away, then the AP reaction is developed using a colored substrate. The assay is quantitated using a spectrophotometer. FIG. 4 shows a typical TIE-2-IgG binding curve. This assay has been used to evaluate the integrity of TIE-2-IgG after injection into rats and mice. The assay can also be used in this format as a ligand competition assay, in which purified or partially-purified TIE ligands compete with immobilized ligand for receptorbody. In the ligand binding and competition version of the binding assay, TIE-2 ectodomain is coated onto the ELISA plate. The Fc-tagged fibrinogen-like domain fragments of the TIE ligands (TL1-fFc and TL2-fFc) then bind to the ectodomain, and can be detected using the same anti-human Fc antibody as described above. FIG. 5 shows an example of TL1-fFc binding to TIE-2 ectodomain. This version of the assay can also be used to quantitate levels of TL1-fFc in serum or other samples. If untagged ligand (again, either purified or unpurified) is added at the same time as the TL1-fFc, then a competition is set up between tagged ligand fragment and full-length ligand. The full-length ligand can displace the Fc-tagged fragment, and a competition curve is generated.

EXAMPLE 9

EA.hy926 Cell Line can be Used as a Reporter Cell Line for TIE Ligand Activity

EA.hy926 is a cell hybrid line that was established by fusion of HUVEC with the human lung carcinoma-derived line, A549 [Edgell, et al. Proc. Natl. Acad. Sci. (USA) 80, 3734–3737 (1983). EA.hy926 cells have been found to express significant levels of TIE-2 receptor protein with low basal phosphotyrosine levels. The density at which EA.hy926 cells are passaged prior to their use for receptor assays, as well as their degree of confluency at the time of assay, can affect TIE-2 receptor abundance and relative inducibility in response to treatment with ligand. By adopting the following regimen for growing these cells the EA.hy926 cell line can be used as a dependable system for assay of TIE-2 ligand activities.

EA.hy926 cells are seeded at $1.5 \times 10^6$ cells in T-75 flasks (Falconware) and re-fed every other day with high-glucose Dulbecco's MEM, 10% fetal bovine serum, L-glutamine, penicillin-streptomycin, and 1×hypoxanthine-aminopterin-thymidine (HAT, Gibco/BRL). After three to four days of growth, the cells are passaged once again at $1.5 \times 10^6$ cells per T-75 flask and cultured an additional three to four days. For phosphorylation assays, cells prepared as described above were serum-starved by replacement of the culture medium with high-glucose DMEM and incubation for 2–3 hours at 37° C. This medium was aspirated from the flask and samples of conditioned media or purified ligand were added to the flask in a total volume of 1.5 ml followed by incubation at 37° C. for 5 minutes. Flasks were removed from the incubator and placed on a bed of ice. The medium was removed and replaced with 1.25 ml Lysis Buffer containing 1% nonidet P-40, 0.5% sodium deoxycholate, 0.1% SDS in 20 mM Tris, pH 7.6, 150 mM NaCl, 50 mM NaF, 1 mM sodium orthovanadate, 5 mM benzamidine, and 1 mM EDTA containing the protease inhibitors PMSF, aprotinin, and leupeptin. After 10 minutes on ice to allow membrane solubilization, plates were scraped and cell lysates were clarified by microcentrifugation at top speed for 10 minutes at 4° C. TIE-2 receptor was immunoprecipitated from the clarified supernatant by incubation in the cold with an anti-TIE-2 polyclonal antiserum and Protein G-conjugated Sepharose beads. The beads were washed three times with cold cell lysis buffer and boiled 5 minutes in Laemmli sample buffer, which was then loaded on 7.5% SDS-polyacrylamide gels. Resolved proteins were electrotransferred to PVDF (Lamblia-P) membrane and then subjected to Western blot analysis using anti-phosphotyrosine antibody and the ECL reagent. Subsequent comparison of total TIE-2 protein levels on the same blots was done by stripping the anti-phosphotyrosine antibody and reincubating with a polyclonal antiserum specific to the ectodomain of TIE-2.

EXAMPLE 10

Isolation and Sequencing of Full Length cDNA Clone Encoding Mammalian TIE Ligand-3

TIE ligand-3 (TL3) was cloned from a mouse BAC genomic library (Research Genetics) by hybridizing library duplicates, with either mouse TL1 or mouse TL2 probes corresponding to the entire coding sequence of those genes. Each copy of the library was hybridized using phosphate buffer at 55° C. overnight. After hybridization, the filters were washed using 2×SSC, 0.1% SDS at 60° C., followed by exposure of X ray film to the filters. Strong hybridization signals were identified corresponding to mouse TL1 and mouse TL2. In addition, signals were identified which weakly hybridized to both mouse TL1 and mouse TL2. DNA corresponding to these clones was purified, then digested with restriction enzymes, and two fragments which hybridized to the original probes were subcloned into a bacterial plasmid and sequenced. The sequence of the fragments contained two exons with homology to both mouse TL1 and mouse TL2. Primers specific for these sequences were used as PCR primers to identify tissues containing transcripts corresponding to TL3. A PCR band corresponding to TL3 was identified in a mouse uterus cDNA library in lambda gt-11. (Clontech Laboratories, Inc., Palo Alto, Calif.).

Plaques were plated at a density of 1.25×10⁶/20×20 cm plate and replica filters taken following standard procedures (Sambrook, et al., Molecular Cloning: A Laboratory Manual, 2nd Ed., page 8.46, Cold Spring Harbor Laboratory, Cold Spring Harbor, N.Y.). Duplicate filters were screened at "normal" stringency (2×SSC, 65° C.) with a 200 bp PCR radioactive probe made to the mouse TL3 sequence. Hybridization was at 65° C. in a solution containing 0.5 mg/ml salmon sperm DNA. Filters were washed in 2×SSC at 65° C. and exposed for 6 hours to X-ray film. Two positive clones that hybridized in duplicate were picked. EcoRI digestion of phage DNA obtained from these clones indicated two independent clones with insert sizes of approximately 1.2 kb and approximately 2.2 kb. The 2.2 kb EcoRI insert was subcloned into the EcoRI site of pBluescript KS (Stratagene). Sequence analysis showed that the longer clone was lacking an initiator methionine and signal peptide but otherwise encoded a probe homologous to both mouse TL1 and mouse TL2.

Two TL3-specific PCR primers were then synthesized as follows:

US2: cctctgggctcgccagtttgttagg (SEQ ID NO: 11)
US1: ccagctggcagatatcagg (SEQ ID NO: 12)

The following PCR reactions were performed using expression libraries derived from the mouse cell lines C2C12ras and MG87. In the primary PCR reaction, the specific primer US2 was used in conjunction with vector-specific oligos to allow amplification in either orientation. PCR was in a total volume of 100 ml using 35 cycles of 94° C., 1 mim; 42° C. or 48° C. for 1 min; 72° C., 1 min. The secondary PCR reaction included the second specific primer, US1, which is contained within the primary PCR product, in conjunction with the same vector oligos. The secondary reactions were for 30 cycles, using the same temperatures and times as previous. PCR products were gel isolated and submitted for sequence analysis. On the basis of sequences obtained from a total of four independent PCR reactions using two different cDNA libraries, the 5' end of the TL3 sequence was deduced. Northern analysis revealed moderate to low levels of mouse TL3 transcript in mouse placenta. The expression of mouse TL3 consisted of a transcript of approximately 3 kb. The full length TL3 coding sequence is set forth in FIGS. 6A–6B (SEQ ID NOS: 1 and 2).

The mouse TL3 sequence may then be used to obtain a human clone containing the coding sequence of its human counterpart by hybridizing either a human genomic or cDNA library with a probe corresponding to mouse TL3 as has been described previously, for example, in Example 8 in International Publication No. WO 96/31598 published 10 Oct. 1996.

EXAMPLE 11

Isolation of Full Length Genomic Clone Encoding Human TIE Ligand-4

TIE ligand-4 (TL4) was cloned from a mouse BAC genomic library (BAC HUMAN (II), Genome Systems Inc.) by hybridizing library duplicates, with either a human TL1 radioactive probe corresponding to the entire fibrinogen coding sequence of TL1 (nucleotides 1153 to 1806) or a mouse TL3 radioactive probe corresponding to a segment of186 nucleotides from the fibrinogen region of mouse TL3 (nucleotides 1307 to 1492 of FIGS. 6A–6B). Each probe was labeled by PCR using exact oligonucleotides and standard PCR conditions, except that dCTP was replaced by $P^{32}$dCTP. The PCR mixture was then passed through a gel filtration column to separate the probe from free $P^{32}$ dCTP. Each copy of the library was hybridized using phosphate buffer, and radiactive probe at 55° C. overnight using standard hybridization conditions. After hybridization, the filters were washed using 2×SSC, 0.1% SDS at 55° C., followed by exposure of X ray film. Strong hybridization signals were observed corresponding to human TL1. In addition, signals were identified which weakly hybridized to both human TL1 and mouse TL3. DNA corresponding to these clones was purified using standard procedures, then digested with restriction enzymes, and one fragment which hybridized to the original probes was subcloned into a bacterial plasmid and sequenced. The sequence of the fragments contained one exon with homology to both human TL1 and mouse TL3 and other members of the TIE ligand family. Primers specific for these sequences may be used as PCR primers to identify tissues containing transcripts corresponding to TL4.

The complete sequence of human TL4 may be obtained by sequencing the full BAC clone contained in the deposited bacterial cells. Exons may be identified by homology to known members of the TIE-ligand family such as TL1, TL2 and TL3. The full coding sequence of TL4 may then be determined by splicing together the exons from the TL4 genomic clone which, in turn, may be used to produce the TL4 protein. Alternatively, the exons may be used as probes to obtain a full length cDNA clone, which may then be used to produce the TL4 protein. Exons may also be identified from the BAC clone sequence by homology to protein domains such as fibrinogen domains, coiled coil domains, or protein signals such as signal peptide sequences. Missing exons from the BAC clone may be obtained by identification of contiguous BAC clones, for example, by using the ends of the deposited BAC clone as probes to screen a human genomic library such as the one used herein, by using the exon sequence contained in the BAC clone to screen a cDNA library, or by performing either 5' or 3' RACE procedure using oligonucleotide primers based on the TL4 exon sequences.

Identification of Additional TIE Ligand Family Members

The novel TIE ligand-4 sequence may be used in a rational search for additional members of the TIE ligand family using an approach that takes advantage of the existence of conserved segments of strong homology between the known family members. For example, an alignment of the amino acid sequences of the TIE ligands shows several regions of conserved sequence (see underlined regions of FIG. 7 [SEQ ID NOS: 3–8]). Degenerate oligonucleotides essentially based on these boxes in combination with either previously known or novel TIE ligand homology segments may be used to identify new TIE ligands.

The highly conserved regions among TL1, TL2 and TL3 may be used in designing degenerate oligonucleotide primers with which to prime PCR reactions using cDNAs. cDNA templates may be generated by reverse transcription of tissue RNAs using oligo d(T) or other appropriate primers. Aliquots of the PCR reactions may then be subjected to electrophoresis on an agarose gel. Resulting amplified DNA fragments may be cloned by insertion into plasmids, sequenced and the DNA sequences compared with those of all known TIE ligands.

Size-selected amplified DNA fragments from these PCR reactions may be cloned into plasmids, introduced into *E. coli* by electroporation, and transformants plated on selective agar. Bacterial colonies from PCR transformation may be analyzed by sequencing of plasmid DNAs that are purified by standard plasmid procedures.

Cloned fragments containing a segment of a novel TIE ligand may be used as hybridization probes to obtain full length cDNA clones from a cDNA library. For example, the human TL4 genomic sequence may be used to obtain a human cDNA clone containing the complete coding sequence of human TL4 by hybridizing a human cDNA library with a probe corresponding to human TL4 as has been described previously.

EXAMPLE 12

Cloning of the Full Coding Sequence of hTL4

Both 5 and 3' coding sequence from the genomic human TL-4 clone encoding human TIE ligand-4 (hTL-4 ATCC Accession No. 98095) was obtained by restriction enzyme digestion, Southern blotting and hybridization of the hTL-4 clone to coding sequences from mouse TL3, followed by subcloning and sequencing the hybridizing fragments. Coding sequences corresponding to the N-terminal and C-terminal amino acids of hTL4 were used to design PCR primers (shown below), which in turn were used for PCR amplification of TL4 from human ovary cDNA. A PCR band was identified as corresponding to human TL4 by DNA sequencing using the ABI 373A DNA sequencer and Taq Dideoxy Terminator Cycle Sequencing Kit (Applied Biosystems, Inc., Foster City, Calif.). The PCR band was then subcloned into vector PCR-script and several plasmid clones were analyzed by sequencing. The complete human TL4 coding sequence was then Compiled and is shown in FIGS. 8A–8C (SEQ ID NOS: 9 and 10). In another embodiment of the invention, the nucleotide at position 569 is changed from A to G, resulting in an amino acid change from Q to R.

The PCR primers used as described above were designed as follows:

hTL4atg 5'-gcatgctatctcgagccaccATGCTCTCCCAGC-TAGCCATGCTGCAG-3' (SEQ ID NO: 13)

hTL4not 5' gtgtcgacgcggccgctctagatcagacTTAGATGT-CCAAAGGCCGTATCATCAT-3' (SEQ ID NO: 14)

DEPOSITS

The following have been deposited with the American Type Culture Collection, 10801 University Boulevard, Manassas, Va. 20110-2209, in accordance with the Budapest Treaty. Recombinant *Autographa californica* baculovirus encoding TIE-2 receptorbody was deposited with the ATCC on Oct. 7, 1994 and designated as "vTIE-2 receptorbody" under ATCC Accession No. VR2484. *E. coli* strain DH10B containing plasmid pBeLoBac11 with a human TL-4 gene insert encoding human TIE ligand-4 was deposited with the ATCC on Jul. 2, 1996 and designated as "hTL-4" under ATCC Accession No. 98095.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

What is claimed is:

1. Isolated TIE ligand-3 as set forth in SEQ ID NO: 2 substantially free of other proteins.

2. Isolated TIE ligand-3 as set forth in SEQ ID NO: 2 encoded by a nucleic acid molecule comprising a nucleotide sequence selected from the group consisting of:
   a) the nucleotide sequence set forth in SEQ ID NO: 1;
   b) a nucleotide sequence that hybridizes in phosphate buffer at 55° C. overnight or in 2×SSC at 65° C. to a nucleotide sequence that is complementary to the nucleotide sequence of (a); and
   c) a nucleotide sequence that, due to the degeneracy of the genetic code, differs from the sequence of (a) or (b) and which encodes TIE ligand-3 as set forth in SEQ ID NO: 2.

3. A conjugate comprising a ligand of claim 1 or 2 conjugated to a cytotoxic agent.

4. A conjugate according to claim 3 wherein the cytotoxic agent is a radioisotope or toxin.

5. A composition comprising the ligand of claim 1 or 2 and a carrier.

6. A composition comprising the conjugate of claim 3 and a carrier.

7. A composition comprising the conjugate of claim 4 and a carrier.

* * * * *

SEQUENCE LISTING

<160> NUMBER OF SEQ ID NOS: 14

<210> SEQ ID NO 1
<211> LENGTH: 1849
<212> TYPE: DNA
<213> ORGANISM: Mus musculus
<220> FEATURE:
<221> NAME/KEY: CDS
<222> LOCATION: (47)..(1573)

<400> SEQUENCE: 1

```
ctgtcctggt acctgacaag accacctcac caccacttgg tctcag atg ctc tgc         55
                                                 Met Leu Cys
                                                   1 cag cca gct atg cta cta gat ggc ctc ctg ctg gcc acc atg gct            103
Gln Pro Ala Met Leu Leu Asp Gly Leu Leu Leu Ala Thr Met Ala
      5                  10                  15 gca gcc cag cac aga ggg cca gaa gcc ggt ggg cac cgc cag att cac        151
Ala Ala Gln His Arg Gly Pro Glu Ala Gly Gly His Arg Gln Ile His
 20                  25                  30                  35 cag gtc cgg cgt ggc cag tgc agc tac acc ttt gtg gtg ccg gag cct        199
Gln Val Arg Arg Gly Gln Cys Ser Tyr Thr Phe Val Val Pro Glu Pro
              40                  45                  50 gat atc tgc cag ctg gcg ccg aca gcg gcg cct gag gct ttg ggg ggc        247
Asp Ile Cys Gln Leu Ala Pro Thr Ala Ala Pro Glu Ala Leu Gly Gly
          55                  60                  65 tcc aat agc ctc cag agg gac ttg cct gcc tcg agg ctg cac cta aca        295
Ser Asn Ser Leu Gln Arg Asp Leu Pro Ala Ser Arg Leu His Leu Thr
     70                  75                  80 gac tgg cga gcc cag agg gcc cag cgg gcc cag cgt gtg agc cag ctg        343
Asp Trp Arg Ala Gln Arg Ala Gln Arg Ala Gln Arg Val Ser Gln Leu
 85                  90                  95 gag aag ata cta gag aat aac act cag tgg ctg ctg aag ctg gag cag        391
Glu Lys Ile Leu Glu Asn Asn Thr Gln Trp Leu Leu Lys Leu Glu Gln
100                 105                 110                 115 tcc atc aag gtg aac ttg agg tca cac ctg gtg cag gcc cag cag gac        439
Ser Ile Lys Val Asn Leu Arg Ser His Leu Val Gln Ala Gln Gln Asp
             120                 125                 130 aca atc cag aac cag aca act acc atg ctg gca ctg ggt gcc aac ctc        487
Thr Ile Gln Asn Gln Thr Thr Thr Met Leu Ala Leu Gly Ala Asn Leu
         135                 140                 145 atg aac cag acc aaa gct cag acc cac aag ctg act gct gtg gag gca        535
Met Asn Gln Thr Lys Ala Gln Thr His Lys Leu Thr Ala Val Glu Ala
     150                 155                 160 cag gtc cta aac cag aca ttg cac atg aag acc caa atg ctg gag aac        583
Gln Val Leu Asn Gln Thr Leu His Met Lys Thr Gln Met Leu Glu Asn
 165                 170                 175 tca ctg tcc acc aac aag ctg gag cgg cag atg ctg atg cag agc cga        631
Ser Leu Ser Thr Asn Lys Leu Glu Arg Gln Met Leu Met Gln Ser Arg
180                 185                 190                 195 gag ctg cag cgg ctg cag ggt cgc aac agg gcc ctg gag acc agg ctg        679
Glu Leu Gln Arg Leu Gln Gly Arg Asn Arg Ala Leu Glu Thr Arg Leu
             200                 205                 210 cag gca ctg gaa gca caa cat cag gcc cag ctt aac agc ctc caa gag        727
Gln Ala Leu Glu Ala Gln His Gln Ala Gln Leu Asn Ser Leu Gln Glu
         215                 220                 225 aag agg gaa caa ctg cac agt ctc ctg ggc cat cag acc ggg acc ctg        775
Lys Arg Glu Gln Leu His Ser Leu Leu Gly His Gln Thr Gly Thr Leu
     230                 235                 240
```

-continued

| | |
|---|---|
| gct aac ctg aag cac aat ctg cac gct ctc agc agc att tcc agc tcc<br>Ala Asn Leu Lys His Asn Leu His Ala Leu Ser Ser Ile Ser Ser Ser<br>245                              250                          255 | 823 |
| ctg cag cag cag cag cag caa ctg acg gag ttt gta cag cgc ctg gta<br>Leu Gln Gln Gln Gln Gln Leu Thr Glu Phe Val Gln Arg Leu Val<br>260                              265                          270                        275 | 871 |
| cgg att gta gcc cag gac cag cat ccg gtt tcc tta aag aca cct aag<br>Arg Ile Val Ala Gln Asp Gln His Pro Val Ser Leu Lys Thr Pro Lys<br>                                      280                          285                          290 | 919 |
| cca gtg ttc cag gac tgt gca gag atc aag cgc tcc ggg gtt aat acc<br>Pro Val Phe Gln Asp Cys Ala Glu Ile Lys Arg Ser Gly Val Asn Thr<br>                    295                          300                          305 | 967 |
| agc ggt gtc tat acc atc tat gag acc aac atg aca aag cct ctc aag<br>Ser Gly Val Tyr Thr Ile Tyr Glu Thr Asn Met Thr Lys Pro Leu Lys<br>          310                        315                          320 | 1015 |
| gtg ttc tgt gac atg gag act gat gga ggt ggc tgg acc ctc atc cag<br>Val Phe Cys Asp Met Glu Thr Asp Gly Gly Gly Trp Thr Leu Ile Gln<br>325                              330                          335 | 1063 |
| cac cgg gag gat gga agc gta aat ttc cag agg acc tgg gaa gaa tac<br>His Arg Glu Asp Gly Ser Val Asn Phe Gln Arg Thr Trp Glu Glu Tyr<br>340                              345                          350                        355 | 1111 |
| aaa gag ggt ttt ggt aat gtg gcc aga gag cac tgg ctg ggc aat gag<br>Lys Glu Gly Phe Gly Asn Val Ala Arg Glu His Trp Leu Gly Asn Glu<br>                    360                          365                          370 | 1159 |
| gct gtg cac cgc ctc acc agc aga acg gcc tac ttg cta cgc gtg gaa<br>Ala Val His Arg Leu Thr Ser Arg Thr Ala Tyr Leu Leu Arg Val Glu<br>                    375                          380                          385 | 1207 |
| ctg cat gac tgg gaa ggc cgc cag acc tcc atc cag tat gag aac ttc<br>Leu His Asp Trp Glu Gly Arg Gln Thr Ser Ile Gln Tyr Glu Asn Phe<br>          390                        395                          400 | 1255 |
| cag ctg ggc agc gag agg cag cgg tac agc ctc tct gtg aat gac agc<br>Gln Leu Gly Ser Glu Arg Gln Arg Tyr Ser Leu Ser Val Asn Asp Ser<br>405                              410                          415 | 1303 |
| agc agt tca gca ggg cgc aag aac agc ctg gct cct cag ggc acc aag<br>Ser Ser Ser Ala Gly Arg Lys Asn Ser Leu Ala Pro Gln Gly Thr Lys<br>420                              425                          430                        435 | 1351 |
| ttc agc acc aaa gac atg gac aat gat aac tgc atg tgt aaa tgt gct<br>Phe Ser Thr Lys Asp Met Asp Asn Asp Asn Cys Met Cys Lys Cys Ala<br>                    440                          445                          450 | 1399 |
| cag atg ctg tct gga ggg tgg tgg ttt gat gcc tgt ggc ctc tcc aac<br>Gln Met Leu Ser Gly Gly Trp Trp Phe Asp Ala Cys Gly Leu Ser Asn<br>                    455                          460                          465 | 1447 |
| ctc aat ggc atc tac tat tca gtt cat cag cac ttg cac aag atc aat<br>Leu Asn Gly Ile Tyr Tyr Ser Val His Gln His Leu His Lys Ile Asn<br>                470                          475                          480 | 1495 |
| ggc atc cgc tgg cac tac ttc cga ggc ccc agc tac tca ctg cac ggc<br>Gly Ile Arg Trp His Tyr Phe Arg Gly Pro Ser Tyr Ser Leu His Gly<br>485                              490                          495 | 1543 |
| aca cgc atg atg ctg agg cca atg ggt gcc tgacacacag ccctgcagag<br>Thr Arg Met Met Leu Arg Pro Met Gly Ala<br>500                              505 | 1593 |
| actgatgccg taggaggatt ctcaacccag gtgactctgt gcacgctggg ccctgcccag | 1653 |
| aaatcagtgc ccagggctca tcttgacatt ctggaacatc ggaaccagct taccttgccc | 1713 |
| ctgaattaca agaattcacc tgcctccctg ttgccctcta attgtgaaat tgctgggtgc | 1773 |
| ttgaaggcac ctgcctctgt ggaaccata ctctttcccc ctcctgctgc atgcccggga | 1833 |
| atccctgcca tgaact | 1849 |

<210> SEQ ID NO 2
<211> LENGTH: 509
<212> TYPE: PRT
<213> ORGANISM: Mus musculus

<400> SEQUENCE: 2

```
Met Leu Cys Gln Pro Ala Met Leu Leu Asp Gly Leu Leu Leu Leu Ala
  1               5                  10                  15

Thr Met Ala Ala Ala Gln His Arg Gly Pro Glu Ala Gly Gly His Arg
             20                  25                  30

Gln Ile His Gln Val Arg Arg Gly Gln Cys Ser Tyr Thr Phe Val Val
         35                  40                  45

Pro Glu Pro Asp Ile Cys Gln Leu Ala Pro Thr Ala Ala Pro Glu Ala
     50                  55                  60

Leu Gly Gly Ser Asn Ser Leu Gln Arg Asp Leu Pro Ala Ser Arg Leu
 65                  70                  75                  80

His Leu Thr Asp Trp Arg Ala Gln Arg Ala Gln Arg Ala Gln Arg Val
                 85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Met Leu Ala Leu Gly
    130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
        195                 200                 205

Thr Arg Leu Gln Ala Leu Glu Ala Gln His Gln Ala Gln Leu Asn Ser
    210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Ile
                245                 250                 255

Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
    290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Gly Trp Thr
                325                 330                 335

Leu Ile Gln His Arg Glu Asp Gly Ser Val Asn Phe Gln Arg Thr Trp
            340                 345                 350

Glu Glu Tyr Lys Glu Gly Phe Gly Asn Val Ala Arg Glu His Trp Leu
        355                 360                 365

Gly Asn Glu Ala Val His Arg Leu Thr Ser Arg Thr Ala Tyr Leu Leu
    370                 375                 380
```

```
Arg Val Glu Leu His Asp Trp Glu Gly Arg Gln Thr Ser Ile Gln Tyr
385                 390                 395                 400

Glu Asn Phe Gln Leu Gly Ser Glu Arg Gln Arg Tyr Ser Leu Ser Val
                405                 410                 415

Asn Asp Ser Ser Ser Ala Gly Arg Lys Asn Ser Leu Ala Pro Gln
            420                 425                 430

Gly Thr Lys Phe Ser Thr Lys Asp Met Asp Asn Asp Asn Cys Met Cys
                435                 440                 445

Lys Cys Ala Gln Met Leu Ser Gly Gly Trp Trp Phe Asp Ala Cys Gly
            450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Arg Gly Pro Ser Tyr Ser
                485                 490                 495

Leu His Gly Thr Arg Met Met Leu Arg Pro Met Gly Ala
                500                 505

<210> SEQ ID NO 3
<211> LENGTH: 509
<212> TYPE: PRT
<213> ORGANISM: Mus musculus

<400> SEQUENCE: 3

Met Leu Cys Gln Pro Ala Met Leu Leu Asp Gly Leu Leu Leu Leu Ala
1               5                   10                  15

Thr Met Ala Ala Ala Gln His Arg Gly Pro Glu Ala Gly Gly His Arg
            20                  25                  30

Gln Ile His Gln Val Arg Arg Gly Gln Cys Ser Tyr Thr Phe Val Val
        35                  40                  45

Pro Glu Pro Asp Ile Cys Gln Leu Ala Pro Thr Ala Ala Pro Glu Ala
    50                  55                  60

Leu Gly Gly Ser Asn Ser Leu Gln Arg Asp Leu Pro Ala Ser Arg Leu
65                  70                  75                  80

His Leu Thr Asp Trp Arg Ala Gln Arg Ala Gln Arg Ala Gln Arg Val
                85                  90                  95

Ser Gln Leu Glu Lys Ile Leu Glu Asn Asn Thr Gln Trp Leu Leu Lys
            100                 105                 110

Leu Glu Gln Ser Ile Lys Val Asn Leu Arg Ser His Leu Val Gln Ala
        115                 120                 125

Gln Gln Asp Thr Ile Gln Asn Gln Thr Thr Met Leu Ala Leu Gly
    130                 135                 140

Ala Asn Leu Met Asn Gln Thr Lys Ala Gln Thr His Lys Leu Thr Ala
145                 150                 155                 160

Val Glu Ala Gln Val Leu Asn Gln Thr Leu His Met Lys Thr Gln Met
                165                 170                 175

Leu Glu Asn Ser Leu Ser Thr Asn Lys Leu Glu Arg Gln Met Leu Met
            180                 185                 190

Gln Ser Arg Glu Leu Gln Arg Leu Gln Gly Arg Asn Arg Ala Leu Glu
        195                 200                 205

Thr Arg Leu Gln Ala Leu Glu Ala Gln His Gln Ala Gln Leu Asn Ser
    210                 215                 220

Leu Gln Glu Lys Arg Glu Gln Leu His Ser Leu Leu Gly His Gln Thr
225                 230                 235                 240

Gly Thr Leu Ala Asn Leu Lys His Asn Leu His Ala Leu Ser Ser Asn
                245                 250                 255
```

-continued

```
Ser Ser Ser Leu Gln Gln Gln Gln Gln Leu Thr Glu Phe Val Gln
            260                 265                 270

Arg Leu Val Arg Ile Val Ala Gln Asp Gln His Pro Val Ser Leu Lys
        275                 280                 285

Thr Pro Lys Pro Val Phe Gln Asp Cys Ala Glu Ile Lys Arg Ser Gly
        290                 295                 300

Val Asn Thr Ser Gly Val Tyr Thr Ile Tyr Glu Thr Asn Met Thr Lys
305                 310                 315                 320

Pro Leu Lys Val Phe Cys Asp Met Glu Thr Asp Gly Gly Trp Thr
            325                 330                 335

Leu Ile Gln His Arg Glu Asp Gly Ser Val Asn Phe Gln Arg Thr Trp
            340                 345                 350

Glu Glu Tyr Lys Glu Gly Phe Gly Asn Val Ala Arg Glu His Trp Leu
            355                 360                 365

Gly Asn Glu Ala Val His Arg Leu Thr Ser Arg Thr Ala Tyr Leu Leu
    370                 375                 380

Arg Val Glu Leu His Asp Trp Glu Gly Arg Gln Thr Ser Ile Gln Tyr
385                 390                 395                 400

Glu Asn Phe Gln Leu Gly Ser Glu Arg Gln Arg Tyr Ser Leu Ser Val
            405                 410                 415

Asn Asp Ser Ser Ser Ala Gly Arg Lys Asn Ser Leu Ala Pro Gln
            420                 425                 430

Gly Thr Lys Phe Ser Thr Lys Asp Met Asp Asn Asp Asn Cys Met Cys
        435                 440                 445

Lys Cys Ala Gln Met Leu Ser Gly Gly Trp Trp Phe Asp Ala Cys Gly
    450                 455                 460

Leu Ser Asn Leu Asn Gly Ile Tyr Tyr Ser Val His Gln His Leu His
465                 470                 475                 480

Lys Ile Asn Gly Ile Arg Trp His Tyr Phe Phe Gly Pro Ser Tyr Ser
            485                 490                 495

Leu His Gly Thr Arg Met Met Leu Arg Pro Met Gly Ala
            500                 505
```

<210> SEQ ID NO 4
<211> LENGTH: 503
<212> TYPE: PRT
<213> ORGANISM: Homo sapiens

<400> SEQUENCE: 4

```
Met Leu Ser Gln Leu Ala Met Leu Gln Gly Ser Leu Leu Leu Val Val
 1               5                  10                  15

Ala Thr Met Ser Val Ala Gln Gln Thr Arg Gln Glu Ala Asp Arg Gly
            20                  25                  30

Cys Glu Thr Leu Val Val Gln His Gly His Cys Ser Tyr Thr Phe Leu
        35                  40                  45

Leu Pro Lys Ser Glu Pro Cys Pro Pro Gly Pro Glu Val Ser Arg Asp
    50                  55                  60

Ser Asn Thr Leu Gln Arg Glu Ser Leu Ala Asn Pro Leu His Leu Gly
 65                  70                  75                  80

Lys Leu Pro Thr Gln Gln Val Lys Gln Leu Glu Gln Ala Leu Gln Asn
                85                  90                  95

Asn Thr Gln Trp Leu Lys Lys Leu Glu Arg Ala Ile Lys Thr Ile Leu
            100                 105                 110

Arg Ser Lys Leu Glu Gln Val Gln Gln Gln Met Ala Gln Asn Gln Thr
```

```
             115                 120                 125
Ala Pro Met Leu Glu Leu Gly Thr Ser Leu Leu Asn Gln Thr Thr Ala
        130                 135                 140
Gln Ile Arg Lys Leu Thr Asp Met Glu Ala Gln Leu Leu Asn Gln Thr
145                 150                 155                 160
Ser Arg Met Asp Ala Gln Met Pro Glu Thr Phe Leu Ser Thr Asn Lys
                165                 170                 175
Leu Glu Asn Gln Leu Leu Leu Gln Arg Gln Lys Leu Gln Gln Leu Gln
            180                 185                 190
Gly Gln Asn Ser Ala Leu Glu Lys Arg Leu Gln Ala Leu Glu Thr Lys
        195                 200                 205
Gln Gln Glu Glu Leu Ala Ser Ile Leu Ser Lys Lys Ala Lys Leu Leu
210                 215                 220
Asn Thr Leu Ser Arg Gln Ser Ala Ala Leu Thr Asn Ile Glu Arg Gly
225                 230                 235                 240
Leu Arg Gly Val Arg His Asn Ser Ser Leu Gln Asp Gln Gln His
                245                 250                 255
Ser Leu Arg Gln Leu Leu Val Leu Leu Arg His Leu Val Gln Glu Arg
            260                 265                 270
Ala Asn Ala Ser Ala Pro Ala Phe Ile Met Ala Gly Glu Gln Val Phe
        275                 280                 285
Gln Asp Cys Ala Glu Ile Gln Arg Ser Gly Ala Ser Ala Ser Gly Val
290                 295                 300
Tyr Thr Ile Gln Val Ser Asn Ala Thr Lys Pro Arg Lys Val Phe Cys
305                 310                 315                 320
Asp Leu Gln Ser Ser Gly Gly Arg Trp Thr Leu Ile Gln Arg Arg Glu
                325                 330                 335
Asn Gly Thr Val Asn Phe Gln Arg Asn Trp Lys Asp Tyr Lys Gln Gly
            340                 345                 350
Phe Gly Asp Pro Ala Gly Glu His Trp Leu Gly Asn Glu Val Val His
        355                 360                 365
Gln Leu Thr Arg Arg Ala Ala Tyr Ser Leu Arg Val Glu Leu Gln Asp
370                 375                 380
Trp Glu Gly His Glu Ala Tyr Ala Gln Tyr Glu His Phe His Leu Gly
385                 390                 395                 400
Ser Glu Asn Gln Leu Tyr Arg Leu Ser Val Val Gly Tyr Ser Gly Ser
                405                 410                 415
Ala Gly Arg Gln Ser Ser Leu Val Leu Gln Asn Thr Ser Phe Ser Thr
            420                 425                 430
Leu Asp Ser Asp Asn Asp His Cys Leu Cys Lys Cys Ala Gln Val Met
        435                 440                 445
Ser Gly Gly Trp Trp Phe Asp Ala Cys Gly Leu Ser Asn Leu Asn Gly
450                 455                 460
Val Tyr Tyr His Ala Pro Asp Asn Lys Tyr Lys Met Asp Gly Ile Arg
465                 470                 475                 480
Trp His Tyr Phe Lys Gly Pro Ser Tyr Ser Leu Arg Ala Ser Arg Met
                485                 490                 495
Met Ile Arg Pro Leu Asp Ile
            500

<210> SEQ ID NO 5
<211> LENGTH: 498
<212> TYPE: PRT
<213> ORGANISM: Homo sapiens
```

<400> SEQUENCE: 5

```
Met Thr Val Phe Leu Ser Phe Ala Phe Leu Ala Ala Ile Leu Thr His
  1               5                  10                  15
Ile Gly Cys Ser Asn Gln Arg Arg Ser Pro Glu Asn Ser Gly Arg Arg
                 20                  25                  30
Tyr Asn Arg Ile Gln His Gly Gln Cys Ala Tyr Thr Phe Ile Leu Pro
             35                  40                  45
Glu His Asp Gly Asn Cys Arg Glu Ser Thr Thr Asp Gln Tyr Asn Thr
         50                  55                  60
Asn Ala Leu Gln Arg Asp Ala Pro His Val Glu Pro Asp Phe Ser Ser
 65                  70                  75                  80
Gln Lys Leu Gln His Leu Glu His Val Met Glu Asn Tyr Thr Gln Trp
                 85                  90                  95
Leu Gln Lys Leu Glu Asn Tyr Ile Val Glu Asn Met Lys Ser Glu Met
                100                 105                 110
Ala Gln Ile Gln Gln Asn Ala Val Gln Asn His Thr Ala Thr Met Leu
            115                 120                 125
Glu Ile Gly Thr Ser Leu Leu Ser Gln Thr Ala Glu Gln Thr Arg Lys
        130                 135                 140
Leu Thr Asp Val Glu Thr Gln Val Leu Asn Gln Thr Ser Arg Leu Glu
145                 150                 155                 160
Ile Gln Leu Leu Glu Asn Ser Leu Ser Thr Tyr Lys Leu Glu Lys Gln
                165                 170                 175
Leu Leu Gln Gln Thr Asn Glu Ile Leu Lys Ile His Glu Lys Asn Ser
            180                 185                 190
Leu Leu Glu His Lys Ile Leu Glu Met Glu Gly Lys His Lys Glu Glu
        195                 200                 205
Leu Asp Thr Leu Lys Glu Glu Lys Glu Asn Leu Gln Gly Leu Val Thr
    210                 215                 220
Arg Gln Thr Tyr Ile Ile Gln Glu Leu Glu Lys Gln Leu Asn Arg Ala
225                 230                 235                 240
Thr Thr Asn Asn Ser Val Leu Gln Lys Gln Gln Leu Glu Leu Met Asp
                245                 250                 255
Thr Val His Asn Leu Val Asn Leu Cys Thr Lys Glu Gly Val Leu Leu
            260                 265                 270
Lys Gly Gly Lys Arg Glu Glu Lys Pro Phe Arg Asp Cys Ala Asp
        275                 280                 285
Val Tyr Gln Ala Gly Phe Asn Lys Ser Gly Ile Tyr Thr Ile Tyr Ile
    290                 295                 300
Asn Asn Met Pro Glu Pro Lys Lys Val Phe Cys Asn Met Asp Val Asn
305                 310                 315                 320
Gly Gly Gly Trp Thr Val Ile Gln His Arg Glu Asp Gly Ser Leu Asp
                325                 330                 335
Phe Gln Arg Gly Trp Lys Glu Tyr Lys Met Gly Phe Gly Asn Pro Ser
            340                 345                 350
Gly Glu Tyr Trp Leu Gly Asn Glu Phe Ile Phe Ala Ile Thr Ser Gln
        355                 360                 365
Arg Gln Tyr Met Leu Arg Ile Glu Leu Met Asp Trp Glu Gly Asn Arg
    370                 375                 380
Ala Tyr Ser Gln Tyr Asp Arg Phe His Ile Gly Asn Glu Lys Gln Asn
385                 390                 395                 400
Tyr Arg Leu Tyr Leu Lys Gly His Thr Gly Thr Ala Gly Lys Gln Ser
```

-continued

```
                405                 410                 415
Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
        450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 6
<211> LENGTH: 498
<212> TYPE: PRT
<213> ORGANISM: Mus musculus

<400> SEQUENCE: 6

Met Thr Val Phe Leu Ser Phe Ala Phe Ala Ala Ile Leu Thr His
 1               5                  10                  15

Ile Gly Cys Ser Asn Gln Arg Arg Asn Pro Glu Asn Gly Gly Arg Arg
                20                  25                  30

Tyr Asn Arg Ile Gln His Gly Gln Cys Ala Tyr Thr Phe Ile Leu Pro
            35                  40                  45

Glu His Asp Gly Asn Cys Arg Glu Ser Ala Thr Glu Gln Tyr Asn Thr
        50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
                100                 105                 110

Ala Gln Ile Gln Gln Asn Ala Val Gln Asn His Thr Ala Thr Met Leu
            115                 120                 125

Glu Ile Gly Thr Ser Leu Leu Ser Gln Thr Ala Glu Gln Thr Arg Lys
        130                 135                 140

Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
                165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
        195                 200                 205

Leu Asp Thr Leu Lys Glu Glu Lys Glu Asn Leu Gln Gly Leu Val Ser
210                 215                 220

Arg Gln Thr Phe Ile Ile Gln Glu Leu Glu Lys Gln Leu Ser Arg Ala
225                 230                 235                 240

Thr Asn Asn Asn Ser Ile Leu Gln Lys Gln Gln Leu Glu Leu Met Asp
                245                 250                 255

Thr Val His Asn Leu Val Ser Leu Cys Thr Lys Glu Gly Val Leu Leu
            260                 265                 270

Lys Gly Gly Lys Arg Glu Glu Glu Lys Pro Phe Arg Asp Cys Ala Asp
```

```
            275                 280                 285
Val Tyr Gln Ala Gly Phe Asn Lys Ser Gly Ile Tyr Thr Ile Tyr Phe
    290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
        355                 360                 365

Arg Gln Tyr Met Leu Arg Ile Glu Leu Met Asp Trp Glu Gly Asn Arg
370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
            420                 425                 430

Asp Asn Cys Met Cys Lys Cys Ala Leu Met Leu Thr Gly Gly Trp Trp
                435                 440                 445

Phe Asp Ala Cys Gly Pro Ser Asn Leu Asn Gly Met Phe Tyr Thr Ala
        450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe

<210> SEQ ID NO 7
<211> LENGTH: 496
<212> TYPE: PRT
<213> ORGANISM: Mus musculus

<400> SEQUENCE: 7

Met Trp Gln Ile Ile Phe Leu Thr Phe Gly Trp Asp Leu Val Leu Ala
  1               5                  10                  15

Ser Ala Tyr Ser Asn Phe Arg Lys Ser Val Asp Ser Thr Gly Arg Arg
                20                  25                  30

Gln Tyr Gln Val Gln Asn Gly Pro Cys Ser Tyr Thr Phe Leu Leu Pro
            35                  40                  45

Glu Thr Asp Ser Cys Arg Ser Ser Ser Pro Tyr Met Ser Asn Ala
        50                  55                  60

Val Gln Arg Asp Ala Pro Leu Asp Tyr Asp Asp Ser Val Gln Arg Leu
65                  70                  75                  80

Gln Val Leu Glu Asn Ile Leu Glu Asn Asn Thr Gln Trp Leu Met Lys
                85                  90                  95

Leu Glu Asn Tyr Ile Gln Asp Asn Met Lys Lys Glu Met Val Glu Ile
                100                 105                 110

Gln Gln Asn Val Val Gln Asn Gln Thr Ala Val Met Ile Glu Ile Gly
            115                 120                 125

Thr Ser Leu Leu Asn Gln Thr Ala Ala Gln Thr Arg Lys Leu Thr Asp
130                 135                 140

Val Glu Ala Gln Val Leu Asn Gln Thr Thr Arg Leu Glu Leu Gln Leu
```

-continued

```
                145                 150                 155                 160
        Leu Gln His Ser Ile Ser Thr Asn Lys Leu Glu Lys Gln Ile Leu Asp
                        165                 170                 175

Gln Thr Ser Glu Ile Asn Lys Leu His Asn Lys Asn Ser Phe Leu Glu
                    180                 185                 190

Gln Lys Val Leu Asp Met Glu Gly Lys His Ser Glu Gln Leu Gln Ser
                195                 200                 205

Met Lys Glu Gln Lys Asp Glu Leu Gln Val Leu Val Ser Lys Gln Ser
            210                 215                 220

Ser Val Ile Asp Glu Leu Glu Lys Lys Leu Val Thr Ala Thr Val Asn
        225                 230                 235                 240

Asn Ser Leu Leu Gln Lys Gln Gln His Asp Leu Met Glu Thr Val Asn
                        245                 250                 255

Ser Leu Leu Thr Met Met Ser Ser Pro Asn Ser Lys Ser Ser Val Ala
                    260                 265                 270

Ile Arg Lys Glu Glu Gln Thr Thr Phe Arg Asp Cys Ala Glu Ile Phe
                275                 280                 285

Lys Ser Gly Leu Thr Thr Ser Gly Ile Tyr Thr Leu Thr Phe Pro Asn
            290                 295                 300

Ser Thr Glu Glu Ile Lys Ala Tyr Cys Asp Met Asp Val Gly Gly Gly
        305                 310                 315                 320

Gly Trp Thr Val Ile Gln His Arg Glu Asp Gly Ser Val Asp Phe Gln
                        325                 330                 335

Arg Thr Trp Lys Glu Tyr Lys Glu Gly Phe Gly Asn Pro Leu Gly Glu
                    340                 345                 350

Tyr Trp Leu Gly Asn Glu Phe Val Ser Gln Leu Thr Gly Gln His Arg
                355                 360                 365

Tyr Val Leu Lys Ile Gln Leu Lys Asp Trp Glu Gly Asn Glu Ala His
            370                 375                 380

Ser Leu Tyr Asp His Phe Tyr Leu Ala Gly Glu Glu Ser Asn Tyr Arg
        385                 390                 395                 400

Ile His Leu Thr Gly Leu Thr Gly Thr Ala Ala Lys Ile Ser Ser Ile
                        405                 410                 415

Ser Gln Pro Gly Ser Asp Phe Ser Thr Lys Asp Ser Asp Asn Asp Lys
                    420                 425                 430

Cys Ile Cys Lys Cys Ser Gln Met Leu Ser Gly Gly Trp Trp Phe Asp
                435                 440                 445

Ala Cys Gly Pro Ser Asn Leu Asn Gly Gln Tyr Tyr Pro Gln Lys Gln
            450                 455                 460

Asn Thr Asn Lys Phe Asn Gly Ile Lys Trp Tyr Tyr Trp Lys Gly Ser
        465                 470                 475                 480

Gly Tyr Ser Leu Lys Ala Thr Thr Met Met Ile Arg Pro Ala Asp Phe
                        485                 490                 495

<210> SEQ ID NO 8
<211> LENGTH: 496
<212> TYPE: PRT
<213> ORGANISM: Homo sapiens

<400> SEQUENCE: 8

Met Trp Gln Ile Val Phe Phe Thr Leu Ser Cys Asp Leu Val Leu Ala
  1               5                  10                  15

Ala Ala Tyr Asn Asn Phe Arg Lys Ser Met Asp Ser Ile Gly Lys Lys
                 20                  25                  30
```

-continued

```
Gln Tyr Gln Val Gln His Gly Ser Cys Ser Tyr Thr Phe Leu Leu Pro
            35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Thr Gln Trp Leu Met Lys
             85                  90                  95

Leu Glu Asn Tyr Ile Gln Asp Asn Met Lys Lys Glu Met Val Glu Ile
            100                 105                 110

Gln Gln Asn Ala Val Gln Asn Thr Ala Val Met Ile Glu Ile Gly
            115                 120                 125

Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
            210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
            290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
            370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
```

```
                  450                 455                 460
Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 9
<211> LENGTH: 1512
<212> TYPE: DNA
<213> ORGANISM: Homo sapiens
<220> FEATURE:
<221> NAME/KEY: CDS
<222> LOCATION: (1)..(1509)

<400> SEQUENCE: 9 atg ctc tcc cag cta gcc atg ctg cag ggc agc ctc ctc ctt gtg gtt    48
Met Leu Ser Gln Leu Ala Met Leu Gln Gly Ser Leu Leu Leu Val Val
  1               5                  10                  15 gcc acc atg tct gtg gct caa cag aca agg cag gag gcg gat agg ggc    96
Ala Thr Met Ser Val Ala Gln Gln Thr Arg Gln Glu Ala Asp Arg Gly
             20                  25                  30 tgc gag aca ctt gta gtc cag cac ggc cac tgt agc tac acc ttc ttg   144
Cys Glu Thr Leu Val Val Gln His Gly His Cys Ser Tyr Thr Phe Leu
         35                  40                  45 ctg ccc aag tct gag ccc tgc cct ccg ggg cct gag gtc tcc agg gac   192
Leu Pro Lys Ser Glu Pro Cys Pro Pro Gly Pro Glu Val Ser Arg Asp
     50                  55                  60 tcc aac acc ctc cag aga gaa tca ctg gcc aac cca ctg cac ctg ggg   240
Ser Asn Thr Leu Gln Arg Glu Ser Leu Ala Asn Pro Leu His Leu Gly
 65                  70                  75                  80 aag ttg ccc acc cag cag gtg aaa cag ctg gag cag gca ctg cag aac   288
Lys Leu Pro Thr Gln Gln Val Lys Gln Leu Glu Gln Ala Leu Gln Asn
                 85                  90                  95 aac acg cag tgg ctg aag aag cta gag agg gcc atc aag acg atc ttg   336
Asn Thr Gln Trp Leu Lys Lys Leu Glu Arg Ala Ile Lys Thr Ile Leu
            100                 105                 110 agg tcg aag ctg gag cag gtc cag cag caa atg gcc cag aat cag acg   384
Arg Ser Lys Leu Glu Gln Val Gln Gln Gln Met Ala Gln Asn Gln Thr
        115                 120                 125 gcc ccc atg cta gag ctg ggc acc agc ctc ctg aac cag acc act gcc   432
Ala Pro Met Leu Glu Leu Gly Thr Ser Leu Leu Asn Gln Thr Thr Ala
    130                 135                 140 cag atc cgc aag ctg acc gac atg gag gct cag ctc ctg aac cag aca   480
Gln Ile Arg Lys Leu Thr Asp Met Glu Ala Gln Leu Leu Asn Gln Thr
145                 150                 155                 160 tca aga atg gat gcc cag atg cca gag acc ttt ctg tcc acc aac aag   528
Ser Arg Met Asp Ala Gln Met Pro Glu Thr Phe Leu Ser Thr Asn Lys
                165                 170                 175 ctg gag aac cag ctg ctg cta cag agg cag aag ctc cag cag ctt cag   576
Leu Glu Asn Gln Leu Leu Leu Gln Arg Gln Lys Leu Gln Gln Leu Gln
            180                 185                 190 ggc caa aac agc gcg ctc gag aag cgg ttg cag gcc ctg gag acc aag   624
Gly Gln Asn Ser Ala Leu Glu Lys Arg Leu Gln Ala Leu Glu Thr Lys
        195                 200                 205 cag cag gag gag ctg gcc agc atc ctc agc aag aag gcg aag ctg ctg   672
Gln Gln Glu Glu Leu Ala Ser Ile Leu Ser Lys Lys Ala Lys Leu Leu
    210                 215                 220 aac acg ctg agc cgc cag agc gcc gcc ctc acc aac atc gag cgc ggc   720
Asn Thr Leu Ser Arg Gln Ser Ala Ala Leu Thr Asn Ile Glu Arg Gly
225                 230                 235                 240
```

```
ctg cgc ggt gtc agg cac aac tcc agc ctc ctg cag gac cag cag cac      768
Leu Arg Gly Val Arg His Asn Ser Ser Leu Leu Gln Asp Gln Gln His
                245                 250                 255 agc ctg cgc cag ctg ctg gtg ttg ttg cgg cac ctg gtg caa gaa agg      816
Ser Leu Arg Gln Leu Leu Val Leu Leu Arg His Leu Val Gln Glu Arg
            260                 265                 270 gct aac gcc tcg gcc ccg gcc ttc ata atg gca ggt gag cag gtg ttc      864
Ala Asn Ala Ser Ala Pro Ala Phe Ile Met Ala Gly Glu Gln Val Phe
        275                 280                 285 cag gac tgt gca gag atc cag cgc tct ggg gcc agt gcc agt ggt gtc      912
Gln Asp Cys Ala Glu Ile Gln Arg Ser Gly Ala Ser Ala Ser Gly Val
    290                 295                 300 tac acc atc cag gtg tcc aat gca acg aag ccc agg aag gtg ttc tgt      960
Tyr Thr Ile Gln Val Ser Asn Ala Thr Lys Pro Arg Lys Val Phe Cys
305                 310                 315                 320 gac ctg cag agc agt gga ggc agg tgg acc ctc atc cag cgc cgt gag     1008
Asp Leu Gln Ser Ser Gly Gly Arg Trp Thr Leu Ile Gln Arg Arg Glu
                325                 330                 335 aat ggc acc gtg aat ttt cag cgg aac tgg aag gat tac aaa cag ggc     1056
Asn Gly Thr Val Asn Phe Gln Arg Asn Trp Lys Asp Tyr Lys Gln Gly
            340                 345                 350 ttc gga gac cca gct ggg gag cac tgg ctg ggc aat gaa gtg gtg cac     1104
Phe Gly Asp Pro Ala Gly Glu His Trp Leu Gly Asn Glu Val Val His
        355                 360                 365 cag ctc acc aga agg gca gcc tac tct ctg cgt gtg gag ctg caa gac     1152
Gln Leu Thr Arg Arg Ala Ala Tyr Ser Leu Arg Val Glu Leu Gln Asp
    370                 375                 380 tgg gaa ggc cac gag gcc tat gcc cag tac gaa cat ttc cac ctg ggc     1200
Trp Glu Gly His Glu Ala Tyr Ala Gln Tyr Glu His Phe His Leu Gly
385                 390                 395                 400 agt gag aac cag cta tac agg ctt tct gtg gtc ggg tac agc ggc tca     1248
Ser Glu Asn Gln Leu Tyr Arg Leu Ser Val Val Gly Tyr Ser Gly Ser
                405                 410                 415 gca ggg cgc cag agc agc ctg gtc ctg cag aac acc agc ttt agc acc     1296
Ala Gly Arg Gln Ser Ser Leu Val Leu Gln Asn Thr Ser Phe Ser Thr
            420                 425                 430 ctt gac tca gac aac gac cac tgt ctc tgc aag tgt gcc cag gtg atg     1344
Leu Asp Ser Asp Asn Asp His Cys Leu Cys Lys Cys Ala Gln Val Met
        435                 440                 445 tct gga ggg tgg tgg ttt gac gcc tgt ggc ctg tcs ssc ctc aac ggc     1392
Ser Gly Gly Trp Trp Phe Asp Ala Cys Gly Leu Xaa Xaa Leu Asn Gly
    450                 455                 460 gtc tac tac cac gct ccc gac aac aag tac aag atg gac ggc atc cgc     1440
Val Tyr Tyr His Ala Pro Asp Asn Lys Tyr Lys Met Asp Gly Ile Arg
465                 470                 475                 480 tgg cac tac ttc aag ggc ccc agc tac tca ctg cgt gcc tct cgc atg     1488
Trp His Tyr Phe Lys Gly Pro Ser Tyr Ser Leu Arg Ala Ser Arg Met
                485                 490                 495 atg ata cgg cct ttg gac atc taa                                     1512
Met Ile Arg Pro Leu Asp Ile
            500

<210> SEQ ID NO 10
<211> LENGTH: 503
<212> TYPE: PRT
<213> ORGANISM: Homo sapiens

<400> SEQUENCE: 10

Met Leu Ser Gln Leu Ala Met Leu Gln Gly Ser Leu Leu Leu Val Val
 1               5                  10                  15
```

-continued

```
Ala Thr Met Ser Val Ala Gln Gln Thr Arg Gln Glu Ala Asp Arg Gly
            20                  25                  30
Cys Glu Thr Leu Val Val Gln His Gly His Cys Ser Tyr Thr Phe Leu
        35                  40                  45
Leu Pro Lys Ser Glu Pro Cys Pro Pro Gly Pro Glu Val Ser Arg Asp
    50                  55                  60
Ser Asn Thr Leu Gln Arg Glu Ser Leu Ala Asn Pro Leu His Leu Gly
65                  70                  75                  80
Lys Leu Pro Thr Gln Gln Val Lys Gln Leu Glu Gln Ala Leu Gln Asn
                85                  90                  95
Asn Thr Gln Trp Leu Lys Lys Leu Glu Arg Ala Ile Lys Thr Ile Leu
            100                 105                 110
Arg Ser Lys Leu Glu Gln Val Gln Gln Met Ala Gln Asn Gln Thr
        115                 120                 125
Ala Pro Met Leu Glu Leu Gly Thr Ser Leu Leu Asn Gln Thr Thr Ala
    130                 135                 140
Gln Ile Arg Lys Leu Thr Asp Met Glu Ala Gln Leu Leu Asn Gln Thr
145                 150                 155                 160
Ser Arg Met Asp Ala Gln Met Pro Glu Thr Phe Leu Ser Thr Asn Lys
                165                 170                 175
Leu Glu Asn Gln Leu Leu Leu Gln Arg Gln Lys Leu Gln Gln Leu Gln
            180                 185                 190
Gly Gln Asn Ser Ala Leu Glu Lys Arg Leu Gln Ala Leu Glu Thr Lys
        195                 200                 205
Gln Gln Glu Glu Leu Ala Ser Ile Leu Ser Lys Lys Ala Lys Leu Leu
    210                 215                 220
Asn Thr Leu Ser Arg Gln Ser Ala Ala Leu Thr Asn Ile Glu Arg Gly
225                 230                 235                 240
Leu Arg Gly Val Arg His Asn Ser Ser Leu Leu Gln Asp Gln Gln His
                245                 250                 255
Ser Leu Arg Gln Leu Leu Val Leu Leu Arg His Leu Val Gln Glu Arg
            260                 265                 270
Ala Asn Ala Ser Ala Pro Ala Phe Ile Met Ala Gly Glu Gln Val Phe
        275                 280                 285
Gln Asp Cys Ala Glu Ile Gln Arg Ser Gly Ala Ser Ala Ser Gly Val
    290                 295                 300
Tyr Thr Ile Gln Val Ser Asn Ala Thr Lys Pro Arg Lys Val Phe Cys
305                 310                 315                 320
Asp Leu Gln Ser Ser Gly Gly Arg Trp Thr Leu Ile Gln Arg Arg Glu
                325                 330                 335
Asn Gly Thr Val Asn Phe Gln Arg Asn Trp Lys Asp Tyr Lys Gln Gly
            340                 345                 350
Phe Gly Asp Pro Ala Gly Glu His Trp Leu Gly Asn Glu Val Val His
        355                 360                 365
Gln Leu Thr Arg Arg Ala Ala Tyr Ser Leu Arg Val Glu Leu Gln Asp
    370                 375                 380
Trp Glu Gly His Glu Ala Tyr Ala Gln Tyr Glu His Phe His Leu Gly
385                 390                 395                 400
Ser Glu Asn Gln Leu Tyr Arg Leu Ser Val Val Gly Tyr Ser Gly Ser
                405                 410                 415
Ala Gly Arg Gln Ser Ser Leu Val Leu Gln Asn Thr Ser Phe Ser Thr
            420                 425                 430
Leu Asp Ser Asp Asn Asp His Cys Leu Cys Lys Cys Ala Gln Val Met
```

-continued

```
                                435                 440                 445
        Ser Gly Gly Trp Trp Phe Asp Ala Cys Gly Leu Xaa Xaa Leu Asn Gly
            450                 455                 460

Val Tyr Tyr His Ala Pro Asp Asn Lys Tyr Lys Met Asp Gly Ile Arg
        465                 470                 475                 480

Trp His Tyr Phe Lys Gly Pro Ser Tyr Ser Leu Arg Ala Ser Arg Met
                            485                 490                 495

Met Ile Arg Pro Leu Asp Ile
                    500

<210> SEQ ID NO 11
<211> LENGTH: 25
<212> TYPE: DNA
<213> ORGANISM: Mus musculus

<400> SEQUENCE: 11
cctctgggct cgccagtttg ttagg                                              25

<210> SEQ ID NO 12
<211> LENGTH: 19
<212> TYPE: DNA
<213> ORGANISM: Mus musculus

<400> SEQUENCE: 12
ccagctggca gatatcagg                                                     19

<210> SEQ ID NO 13
<211> LENGTH: 47
<212> TYPE: DNA
<213> ORGANISM: Homo sapiens

<400> SEQUENCE: 13
gcatgctatc tcgagccacc atgctctccc agctagccat gctgcag                      47

<210> SEQ ID NO 14
<211> LENGTH: 55
<212> TYPE: DNA
<213> ORGANISM: Homo sapiens

<400> SEQUENCE: 14
gtgtcgacgc ggccgctcta gatcagactt agatgtccaa aggccgtatc atcat            55
```